United States Patent
Lee et al.

(10) Patent No.: US 9,784,749 B2
(45) Date of Patent: Oct. 10, 2017

(54) BIOMARKER FOR CARDIAC DISORDERS

(71) Applicant: Otago Innovation Limited, Dunedin (NZ)

(72) Inventors: Jacqueline Amanda Lee, Christchurch (NZ); Christopher Joseph Pemberton, Christchurch (NZ)

(73) Assignee: Otago Innovation Limited, Dunedin (NZ)

( * ) Notice: Subject to any disclaimer, the term of this patent is extended or adjusted under 35 U.S.C. 154(b) by 0 days.

(21) Appl. No.: 15/036,748

(22) PCT Filed: Nov. 14, 2014

(86) PCT No.: PCT/NZ2014/000234
§ 371 (c)(1),
(2) Date: May 13, 2016

(87) PCT Pub. No.: WO2015/072865
PCT Pub. Date: May 21, 2015

(65) Prior Publication Data
US 2016/0299154 A1    Oct. 13, 2016

Related U.S. Application Data

(60) Provisional application No. 61/904,957, filed on Nov. 15, 2013.

(51) Int. Cl.
| | |
|---|---|
| G01N 33/53 | (2006.01) |
| G01N 33/68 | (2006.01) |
| C07K 16/18 | (2006.01) |
| C07K 14/47 | (2006.01) |

(52) U.S. Cl.
CPC ..... G01N 33/6893 (2013.01); C07K 14/4716 (2013.01); C07K 16/18 (2013.01); G01N 33/6887 (2013.01); *C07K 2317/33* (2013.01); *C07K 2317/34* (2013.01); *G01N 2333/4712* (2013.01); *G01N 2800/32* (2013.01); *G01N 2800/50* (2013.01); *G01N 2800/52* (2013.01)

(58) Field of Classification Search
None
See application file for complete search history.

(56) References Cited

U.S. PATENT DOCUMENTS

| | | |
|---|---|---|
| 6,376,206 B1 | 4/2002 | Katus et al. |
| 2012/0129198 A1 | 5/2012 | Buechler et al. |

FOREIGN PATENT DOCUMENTS

| | | |
|---|---|---|
| EP | 2 261 669 A1 | 12/2010 |
| WO | 2008/030122 A1 | 3/2008 |
| WO | 2013/017690 A2 | 2/2013 |

OTHER PUBLICATIONS

Aldous et al., "High-sensitivity troponin T for early rule-out of myocardial infarction in recent onset chest pain," *Emerg Med J* 29:805-810, 2012.
International Search Report, mailed Jan. 23, 2015, for International Application No. PCT/NZ2014/000234, 11 pages.
Pemberton et al., "Abstract 9552: A Novel Human Cardiac Troponin T upstream Open Reading Frame Peptide Assists in the Diagnosis and Prognosis of NSTEMI Patients," *Circulation* 128(Suppl 22): 2003, 2 pages.
Pemberton et al., "A novel troponin T peptide in acute breathless patients presenting to ED," *European Heart Journal* 35:1180, 2014, 1 page.

*Primary Examiner* — Jacob Cheu
(74) *Attorney, Agent, or Firm* — Seed IP Law Group LLP

(57) ABSTRACT

The present invention relates generally to assays, methods and kits for the prognosis and/or diagnosis of cardiac disorders. The present invention also provides, for example, binding agents to a novel class of circulating cardiac troponin T upstream open reading frame (TnTuORF) peptide biomarkers for use in predicting or diagnosing a cardiac disorder other than myocardial infarction or unstable angina. In addition, the binding agents of the present invention may be used to enhance the sensitivity and false positive performance of cardiac troponins in the prognosis and diagnosis of myocardial infarction.

12 Claims, 9 Drawing Sheets

BIOMARKER FOR CARDIAC DISORDERS

STATEMENT REGARDING SEQUENCE LISTING

The Sequence Listing associated with this application is provided in text format in lieu of a paper copy, and is hereby incorporated by reference into the specification. The name of the text file containing the Sequence Listing is 720125_402USPC_SEQUENCE_LISTING.txt. The text file is 1.1 KB, was created on May 18, 2017, and is being submitted electronically via EFS-Web.

TECHNICAL FIELD

The present invention relates generally to methods, assays and kits for the prognosis and/or diagnosis of cardiac disorders.

BACKGROUND OF THE INVENTION

The following includes information that may be useful in understanding the present invention. It is not an admission that any of the information, publications or documents specifically or implicitly referred to or referenced herein is prior art, or essential, to the presently described or claimed inventions. All publications and patents mentioned in this specification are incorporated herein by reference in their entirety.

The advent of highly sensitive (hs) assays for the detection of cardiac troponins (cTn) has significantly altered our understanding of troponin in the circulation and altered aspects of its use for the diagnosis of acute myocardial infarction (MI; Thygesen et al. (2012) *Circulation* 126: 2020-2035; Keller et al. (2009) *N. Eng. J. Med.* 361:868-877; Reichlin et al. (2009) *N. Eng. J. Med.* 361:858-867). These assays have resulted in major improvements in time to diagnosis of myocardial infarction (MI), but this has come at the cost of increasing numbers of patients who have elevated levels of troponin above 99th percentile guidelines, but do not in fact have MI (Reichlin et al. (2012) *Am. J. Med.* 125:1205-1213; Thygesen et al. (2012) *Eur. Heart J.* 33:2252-2257; Hammerer-Lercher et al. (2013) *J. Am. Heart Assoc.* 2(3):e000204.doi:10.1161/JAHA.113.000204). This imbues significant reductions in assay specificity and as a consequence several biomarker based strategies have been suggested to help hscTn measurement (Eggers et al, (2008) *Eur. Heart J.* 29:2327-2335; Haaf et al. (2011) *Am. J. Med.* 124:731-739; Maisel et al. (2013) *J. Am. Coll. Cardiol.* 62:150-160; Cullen et al. (2013) *J. Am. Coll. Cardiol.* 62:1242-1249). One potential strategy to overcome these limitations is consideration of total potential cardiac troponin produced, including upstream open reading frame peptides.

Upstream open reading frames (uORFs) are amino acid coding sequences defined by a start and stop codons upstream (5') of the main coding region in proteins. Approximately 40-50% of the human and mouse transcriptome contain uORFs (Calvo et al. (2009) *Proc. Natl. Acad. Sci.* 106:7507-7512; Iacono et al. (2005) *Gene* 349:97-105) and they are less frequent than expected by chance (Neafsey et al. (2007) *Mol. Biol. Evol.* 24:1744-1751) suggesting they are under selective pressure. However, uORFs are overrepresented in the protein subgroup containing transcription factors, growth factors, proto-oncogenes and their receptors (Davuluri et al. (2000) *Genome Res.* 10:1807-1816). Adding to their complexity, uORFs are extremely diverse varying in position in relation to the cap and main ORF AUG, number per transcript and length (Calvo et al. (2009) *Proc. Natl. Acad. Sci.* 106:7507-7512; Somers et al, (2013) *Int. J. Biochem. Cell Biol.* 45:1690-1700). In mammalian cells there is limited experimental evidence concerning direct translational actions of uORFs upon cellular function and there is no evidence that uORF-derived peptides are present in the circulation. A single report has documented that the glucocorticoid receptor transcript 1A (GR-1A) possesses 5 uORF start sites in its 1026 bp 5'-UTR. One of these uORFs encodes a 93 amino acid peptide that was detected in the nucleus, cytosol and plasma membrane of mouse and human cell cultures and was found to play a role in promoting GR-1A translation (Diba et al. (2001) *J. Cell. Biochem.* 81:149-161).

The Applicants demonstrate here that uORF peptides are present in the 5'-UTR of the human cardiac troponin T (TnT) gene and surprisingly provide the first direct evidence to demonstrate that a cardiac TnTuORF peptide is indeed present in the human circulation and that its assay quantitation has utility in the prognosis and diagnosis of cardiac disorders, and in improving the sensitivity and false positive performance of established biomarkers for cardiac disease, including myocardial infarction.

SUMMARY OF THE INVENTION

The inventions described and claimed herein have many attributes and embodiments including, but not limited to, those set forth or described or referenced in this Summary of the Invention. It is not intended to be all-inclusive and the inventions described and claimed herein are not limited to or by the features or embodiments identified in this Summary of the Invention, which is included for purposes of illustration only and not restriction.

The present invention relates generally to assays, methods and kits for the prognosis and/or diagnosis of cardiac disorders. In particular, the present invention relates to the use of a novel class of circulating biomarker encoded for by an upstream open reading frame of Troponin T and binding agents specific to this peptide in assays, methods and kits for the prognosis and/or diagnosis of, for example, cardiac disorders other than myocardial infarction or unstable angina.

In one aspect of the present invention there is provided a method of predicting a subject's risk of acquiring a cardiac disorder other than myocardial infarction or unstable angina, the method comprising:

(i) measuring the level of a Troponin T upstream open reading frame (TnTuORF) peptide in a biological sample from the subject; and (ii) comparing the measured level of the TnTuORF peptide against a reference interval from a suitable control population, wherein an increase in the circulating level of the TnTuORF peptide compared with the control population is predictive of acquiring a cardiac disorder other than myocardial infarction or unstable angina, and further wherein the measuring step comprises detecting binding between the TnTuORF peptide and a binding agent that selectively binds to the TnTuORF peptide.

In one embodiment, the method further comprises the step of (iii) administering a treatment regime to the subject where the subject is found to have an increase in the circulating level of the TnTuORF peptide compared with the level of the circulating TnTuORF peptide from the control population.

In another embodiment, the method further comprises measuring the level of the TnTuORF peptide in a first biological sample from the subject and measuring the level of the TnTuORF peptide in a second biological sample, wherein the second biological sample is taken from the same subject as the first biological sample but at a later period in time, and comparing the levels of TnTuORF peptide in the first and second samples, wherein an increase in the circulating level of TnTuORF peptide between the first and second samples is indicative of increased risk to acquiring a cardiac disorder other than myocardial infarction or unstable angina.

In another aspect of the present invention there is provided a method of diagnosing a cardiac disorder other than myocardial infarction or unstable angina in a subject, the method comprising:
(i) measuring the level of a Troponin T upstream open reading frame (TnTuORF) peptide in a biological sample from the subject; and
(ii) comparing the measured level of the TnTuORF peptide against a reference interval from a suitable control population,
wherein an increase in the circulating level of the TnTuORF peptide compared with the control population is indicative of a cardiac disorder other than myocardial infarction or unstable angina, and further wherein the measuring step comprises detecting binding between the TnTuORF peptide and a binding agent that selectively binds to the TnTuORF peptide.

In one embodiment, the method further comprises the step of (iii) administering a treatment regime to the subject where the subject is found to have an increase in the circulating level of the TnTuORF peptide compared with the level of the circulating TnTuORF peptide from the control population.

In another embodiment according to any aspect of the present invention, measuring TnTuORF peptide in a biological sample may occur more than once. For example, one, two, three, four, five, ten, fifteen etc measurements may be performed over a period of time spanning hours, days, weeks, months or years.

In a further embodiment, the method comprises measuring the level of the TnTuORF peptide in a first biological sample from the subject and measuring the level of the TnTuORF peptide in a second biological sample, wherein the second biological sample is taken from the same subject as the first biological sample but at a later period in time, and comparing the levels of the TnTuORF peptide in the first and second samples, wherein an increase in the circulating level of the TnTuORF peptide between the first and second samples is indicative of a cardiac disorder other than myocardial infarction or unstable angina and/or persistence of a cardiac disorder other than myocardial infarction or unstable angina.

In certain embodiments according to any aspect of the present invention, the cardiac disorder other than myocardial infarction or unstable angina includes, for example, atrial fibrilation, heart failure, pericarditis, vasovagalsyncope, disorders of nerve conduction and combinations thereof.

In yet another aspect of the present invention there is provided a method for monitoring the responsiveness of a subject to treatment with a drug or therapy for a cardiac disorder other than myocardial infarction or unstable angina, the method comprising:
(i) measuring the level of a TnTuORF peptide in a first biological sample from the subject;
(ii) measuring the level of a TnTuORF peptide in a second biological sample from the subject, wherein the second biological sample is taken from the same subject; and
(iii) comparing the measured levels of the TnTuORF peptide in the first and second samples,
wherein an increase in the level of TnTuORF peptide between the first and second samples is indicative of a poor response to treatment with a with a drug or therapy for a cardiac disorder other than myocardial infarction or unstable angina and wherein a decrease in the level of TnTuORF peptide between the first and second samples is indicative of a positive response to a to treatment with a with a drug or therapy for a cardiac disorder other than myocardial infarction or unstable angina.

Contingent on the cardiac disorder to be treated, it is possible that an increased level of TnTuORF peptide between the first and second samples is indicative of a positive response to treatment with a drug or therapy for a cardiac disorder other than myocardial infarction or unstable angina. Put another way, a decreased level of TnTuORF peptide between the first and second samples is indicative of a poor response to treatment with a drug or therapy for a cardiac disorder other than myocardial infarction or unstable angina.

Accordingly, in yet a further aspect of the present invention there is provided a method for monitoring the responsiveness of a subject to treatment with a drug or therapy for a cardiac disorder other than myocardial infarction or unstable angina, the method comprising:
(i) measuring the level of a TnTuORF peptide in a first biological sample from the subject;
(ii) measuring the level of a TnTuORF peptide in a second biological sample from the subject, wherein the second biological sample is taken from the same subject; and
(iii) comparing the measured levels of the TnTuORF peptide in the first and second samples,
wherein an decrease in the level of TnTuORF peptide between the first and second samples is indicative of a poor response to treatment with a with a drug or therapy for a cardiac disorder other than myocardial infarction or unstable angina and wherein an increase in the level of TnTuORF peptide between the first and second samples is indicative of a positive response to a to treatment with a with a drug or therapy for a cardiac disorder other than myocardial infarction or unstable angina.

In other embodiments according to any method disclosed herein, the measuring step comprises detecting binding between a TnTuORF peptide and a binding agent that selectively binds to the TnTuORF peptide. In one embodiment, the binding agent is an antibody or antigen-binding fragment thereof. In another embodiment, the antibody is a monoclonal antibody or antigen-binding fragment thereof. In other embodiments, binding to the TnTuORF peptide is measured using antibodies that are immobilised to a solid phase.

In a further aspect of the present invention there is provided an assay for measuring the level of a Troponin T upstream open reading frame (TnTuORF) peptide in a biological sample from a subject with, or at risk of acquiring, a cardiac disorder other than myocardial infarction or unstable angina, comprising a binding agent that selectively binds to a TnTuORF peptide and which binding agent can be quantatively measured upon binding to the TnTuORF peptide.

In yet a further aspect of the present invention there is provided a kit for measuring the level of a Troponin T upstream open reading frame (TnTuORF) peptide in a biological sample from a subject with, or at risk of acquiring, a cardiac disorder other than myocardial infarction or unstable angina, comprising a binding agent that selectively binds to a TnTuORF peptide and which binding agent can be quantatively measured upon binding to TnTuORF.

In another aspect of the present invention there is provided a Troponin T upstream open reading frame (TnTuORF) peptide binding agent that selectively binds a TnTuORF peptide for use in predicting a subject's risk of acquiring a cardiac disorder other than myocardial infarction or unstable angina.

In yet a further aspect of the present invention there is provided a Troponin T upstream open reading frame (TnTuORF) peptide binding agent that selectively binds a TnTuORF peptide for use in diagnosing a cardiac disorder other than myocardial infarction or unstable angina in a subject.

In another aspect of the present invention there is provided a use of a Troponin T upstream open reading frame (TnTuORF) peptide binding agent that selectively binds to a TnTuORF peptide in the manufacture of a medicament for predicting a subject's risk for acquiring a cardiac disorder other than myocardial infarction or unstable angina.

In yet another aspect of the present invention there is provided a use of a Troponin T upstream open reading frame (TnTuORF) peptide binding agent that selectively binds to a TnTuORF peptide in the manufacture of a medicament for diagnosing a cardiac disorder other than myocardial infarction or unstable angina in a subject.

In a further aspect of the present invention there is provided an isolated Troponin T upstream open reading frame (TnTuORF) peptide.

In one embodiment, the TnTuORF peptide is selected from the group of peptides set forth in any one of SEQ ID NOs: 1, 2, 3 or 4.

In another aspect of the present invention there is provided an assay for improving the sensitivity and false positive performance of cardiac troponin in predicting a subject's risk of myocardial infarction, the assay comprising a binding agent that selectively binds to a Troponin T upstream open reading frame (TnTuORF) peptide and which binding agent can be quantatively measured upon binding to the TnTuORF peptide in a biological sample from the subject.

In yet a further aspect of the present invention there is provided an assay for improving the sensitivity and false positive performance of cardiac troponin in diagnosing myocardial infarction in a subject, the assay comprising a binding agent that selectively binds to a Troponin T upstream open reading frame (TnTuORF) peptide and which binding agent can be quantatively measured upon binding to the TnTuORF peptide in a biological sample from the subject.

In one embodiment according to either aspect, the cardiac troponin comprises Troponin T and Troponin I. In another embodiment, the assay comprises calculating the product ratio between cardiac troponin and TnTuORF peptide.

In yet a further aspect of the present invention there is provided an assay for predicting mortality in a subject following a cardiac event, the assay comprising a binding agent that selectively binds to a Troponin T upstream open reading frame (TnTuORF) peptide and which binding agent can be quantatively measured upon binding to the TnTuORF peptide in a biological sample from the subject.

In yet another aspect of the present invention there is provided an assay for improving the sensitivity and false positive performance of N-terminal brain natriuretic peptide (NT-proBNP) in predicting a subject's risk of acquiring acute decompensated heart failure following a cardiac event, the assay comprising a binding agent that selectively binds to a Troponin T upstream open reading frame (TnTuORF) peptide and which binding agent can be quantatively measured upon binding to the TnTuORF peptide in a biological sample from the subject.

In a further aspect of the present invention there is provided a kit for measuring the level of a Troponin T upstream open reading frame (TnTuORF) peptide in a biological sample from a subject for use in improving the sensitivity and false positive performance of cardiac troponin in predicting or diagnosing myocardial infarction in the subject, the kit comprising a binding agent that selectively binds to a TnTuORF peptide and which binding agent can be quantatively measured upon binding to TnTuORF.

In a further aspect of the present invention there is provided a kit for measuring the level of a Troponin T upstream open reading frame (TnTuORF) peptide in a biological sample from a subject for use in improving the sensitivity and false positive performance of N-terminal brain natriuretic peptide (NT-proBNP) in predicting the subject's risk of acquiring acute decompensated heart failure following a cardiac event, the kit comprising a binding agent that selectively binds to a TnTuORF peptide and which binding agent can be quantatively measured upon binding to TnTuORF.

In yet a further aspect of the present invention there is provided a Troponin T upstream open reading frame (TnTuORF) peptide binding agent that selectively binds to a TnTuORF peptide in a biological sample from a subject for use in improving the sensitivity and false positive performance of cardiac troponin in predicting or diagnosing myocardial infarction in the subject.

In yet a further aspect of the present invention there is provided a Troponin T upstream open reading frame (TnTuORF) peptide binding agent that selectively binds to a TnTuORF peptide in a biological sample from a subject for use in predicting mortality of the subject following a cardiac event.

In yet a further aspect of the present invention there is provided a Troponin T upstream open reading frame (TnTuORF) peptide binding agent that selectively binds to a TnTuORF peptide in a biological sample from a subject for use in improving the sensitivity and false positive performance of N-terminal brain natriuretic peptide (NT-proBNP) in predicting the subject's risk of acquiring acute decompensated heart failure following a cardiac event.

DEFINITIONS

General

Figure 1:
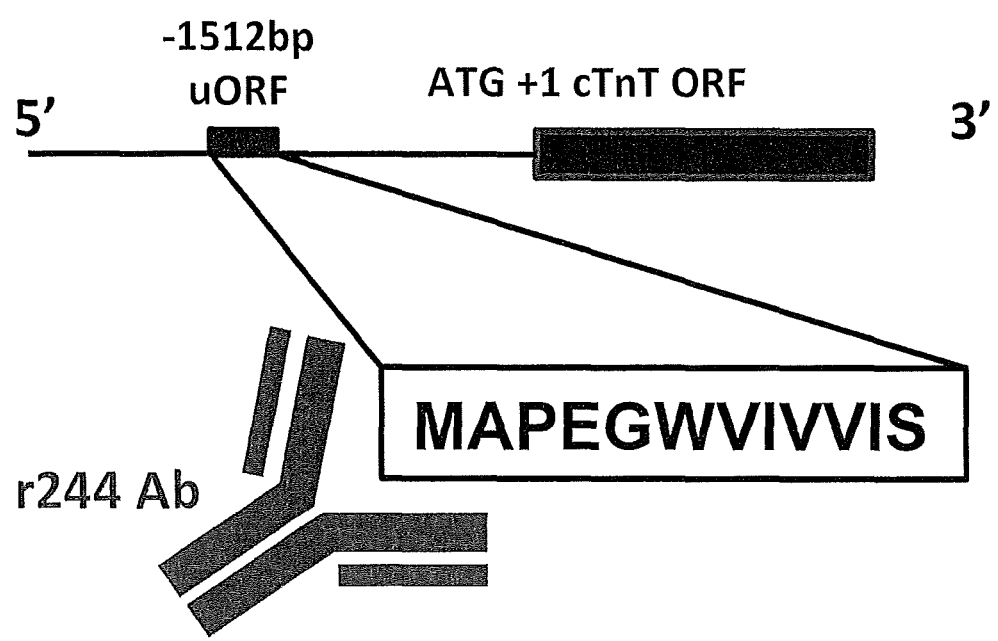
FIG. 1 shows gene location and epitope design of TnTuORF and r244 antiserum. The major open reading frame (ORF) encoding human cardiac troponin T (NCBI Accession NG_007556) is indicated by (ATG+1 cTnT ORF). At −1512 base pairs (bp) 5' upstream from the cTnT ORF there is a uORF encoding a putative 12 amino acid peptide (TnTuORF) with the sequence MAPEGWVIVVIS (SEQ ID NO: 1). Applicants generated a polyclonal antiserum in rabbit (r244) directed to the amino terminus of TnTuORF for use in immunoassay.

Unless specifically defined otherwise, all technical and scientific terms used herein shall be taken to have the same meaning as commonly understood by one of ordinary skill in the art to which the inventions belong (for example, in immunology, immunohistochemistry, protein chemistry, and biochemistry).

Unless otherwise indicated, the recombinant protein and immunological techniques utilized in the present invention are standard procedures well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbor Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al., (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbor Laboratory, (1988), and J. E. Coligan et al., (editors) Current Protocols in Immunology, John Wiley & Sons (including all updates until present).

The term "and/or", e.g., "X and/or Y" shall be understood to mean either "X and Y" or "X or Y" and shall be taken to provide explicit support for both meanings or for either meaning.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

It is intended that reference to a range of numbers disclosed herein (for example 1 to 10) also incorporates reference to all related numbers within that range (for example, 1, 1.1, 2, 3, 3.9, 4, 5, 6, 6.5, 7, 8, 9 and 10) and also any range of rational numbers within that range (for example 2 to 8, 1.5 to 5.5 and 3.1 to 4.7) and, therefore, all sub-ranges of all ranges expressly disclosed herein are expressly disclosed. These are only examples of what is specifically intended and all possible combinations of numerical values between the lowest value and the highest value enumerated are to be considered to be expressly stated in this application in a similar manner.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific embodiments described herein, which are intended for the purpose of exemplification only. Functionally-equivalent products, compositions and methods are clearly within the scope of the invention, as described herein.

Any embodiment herein shall be taken to apply *mutatis mutandis* to any other embodiment unless specifically stated otherwise.

Selected Definitions

Throughout this specification, the term "TnTuORF" means a Troponin T upstream open reading frame peptide. In this specification the terms "TnTuORF" and "TnTuORF peptide" are used interchangeably, and are intended to mean any peptide which exists in circulation as a discrete chemical entity, and is encoded for by an upstream open reading frame of the Troponin T gene.

The term "cardiac disorder other than acute myocardial infarction or unstable angina" according to the present invention includes any cardiac disorder other than myocardial infarction or unstable angina, and includes, for example, atrial fibrillation, heart failure, pericarditis, disorders of nerve conduction and combinations thereof.

The term "biological sample" as used herein includes biological fluids selected from blood including venous blood and arterial blood, plasma, serum, intertistial fluid, or any other body fluid. The term "biological sample" also includes heart tissue sample. The term "biological sample" and "body fluid sample" as used herein refers to a biological sample or a sample of bodily fluid obtained for the purpose of, for example, diagnosis, prognosis, classification or evaluation of a subject of interest, such as a patient. In certain embodiments, such a sample may be obtained for diagnosing a cardiac disorder other than myocardial infarction or unstable angina, for performing risk stratification of a cardiac disorder other than myocardial infarction or unstable angina, for making a prognosis of a disease course in a patient with a cardiac disorder other than myocardial infarction or unstable angina, for identifying a patient with elevated risk of a cardiac disorder other than myocardial infarction or unstable angina, or combinations thereof. In addition, one of skill in the art would realise that certain body fluid samples would be more readily analysed following a fractionation or purification procedure, for example, separation of whole blood into serum or plasma components.

The term "level" as used herein is intended to refer to the amount per weight or weight per weight of TnTuORF. It is also intended to encompass "concentration" expressed as amount per volume or weight per volume. The term "circulating level" is intended to refer to the amount per weight or weight per weight or concentration of a TnTuORF peptide present in the circulating fluid.

An "increase" or "decrease" in the circulating level of a TnTuORF peptide (or any other biomarker for that matter) compared with a control, or a "change" or "deviation" from a control (level) in one embodiment is statistically significant. A increased level, decreased level, deviation from, or change from a control level or mean or historical control level can be considered to exist if the level differs from the control level by about 5% or more, by about 10% or more, by about 20% or more, or by about 50% or more compared to the control level. Statistically significant may alternatively be calculated as P≤0.05. Increased levels, decreased levels, deviation, and changes can also be determined by recourse to assay reference limits or reference intervals. These can be calculated from intuitive assessment or non-parametric methods. Overall, these methods may calculate the 0.025, and 0.975 fractiles as 0.025* (n+1) and 0.975 (n+1). Such methods are well known in the art. Presence of a marker absent in a control may be seen as a higher level, deviation or change. Absence of a marker present in a control may be seen as a lower level, deviation or change.

Specifically, the term "reference interval" as used herein is intended to refer to a figure within a statistical band of a representative concentration or alternatively a figure with an upper or lower concentration. The reference interval will typically be obtained from subjects that do not have any pre-existing conditions that could result in artificially elevating the level of circulating TnTuORF. These conditions are discussed elsewhere herein.

The term "delta %" as used herein is understood to refer to a percentage change in a given variable (i.e. the level or concentration of TnTuORF peptide). The delta % is determined by taking the final concentration of TnTuORF peptide in a biological sample, subtracting the initial concentration of TnTuORF peptide and dividing it by the initial concentration of TnTuORF peptide where the result is presented as a percentage. Thus, by way of non-limiting example, an increase of 300 pmol/mL from an initial concentration of 800 pmol/mL represents a 37.5% change.

For the sake of clarity, an increase of 31-39 delta % includes for example, 31, 32, 33, 34, 35, 36, 37, 38 or 39 delta % increase, as well as fractions there between.

The term "subject" as used herein is intended to refer to a human or non-human primate. In one embodiment, the subject is a human.

The term "suitable control population" according to the present invention refers to the mean circulating TnTuORF peptide level from sex- and age-matched subjects for which cardiac disorder information is known. The control population is used to provide a suitable reference interval by which a measured TnTuORF peptide level is compared.

The term "binding agent" as used herein is intended to refer to any molecule that binds TnTuORF peptides, including small molecules, antibodies from any species whether polyclonal or monoclonal, antigen-binding fragments such as Fab and $Fab_2$, humanized antibodies, chimeric antibodies, or antibodies modified in other ways including substitution of amino acids, and/or fusion with other peptides or proteins (e.g. PEG). It also includes receptors or binding proteins from any species or modified forms of them. In one example, the binding agent specifically binds to TnTuORF.

The term "specifically binds" as used herein shall be taken to mean that the binding agent reacts or associates more frequently, more rapidly, with greater duration and/or with greater affinity to a particular substance than it does with alternative substances. For example, a binding agent that specifically binds to TnTuORF binds that protein or an epitope or immunogenic fragment thereof with greater affinity, avidity, more readily, and/or with greater duration than it binds to unrelated protein and/or epitopes or immunogenic fragments thereof. It is also understood by reading this definition that, for example, a binding agent that specifically binds to a first target (e.g. TnTuORF) may or may not specifically bind to a second target. As such, "specific binding" does not necessarily require exclusive binding or non-detectable binding of another molecule. Generally, but not necessarily, reference to binding means specific binding.

The term "antibody" refers to an immunoglobulin molecule capable of specifically binding to a target, such as TnTuORF by virtue of an antigen binding site contained within at least one variable region. This term includes four chain antibodies (e.g., two light chains and two heavy chains), recombinant or modified antibodies (e.g., chimeric antibodies, humanized antibodies, primatized antibodies, de-immunized antibodies, half antibodies, bispecific antibodies) and single domain antibodies such as domain antibodies and heavy chain only antibodies (e.g., camelid antibodies or cartilaginous fish immunoglobulin new antigen receptors (IgNARs)). An antibody generally comprises constant domains, which can be arranged into a constant region or constant fragment or fragment crystallisable (Fc). Preferred forms of antibodies comprise a four-chain structure as their basic unit. Full-length antibodies comprise two heavy chains (~50-70 kDa) covalently linked and two light chains (~23 kDa each). A light chain generally comprises a variable region and a constant domain and in mammals is either a κ light chain or a λ light chain. A heavy chain generally comprises a variable region and one or two constant domain(s) linked by a hinge region to additional constant domain(s). Heavy chains of mammals are of one of the following types α, δ, ε, γ, or μ. Each light chain is also covalently linked to one of the heavy chains. For example, the two heavy chains and the heavy and light chains are held together by inter-chain disulfide bonds and by non-covalent interactions. The number of inter-chain disulfide bonds can vary among different types of antibodies. Each chain has an N-terminal variable region ($V_H$ or $V_L$ wherein each are ~110 amino acids in length) and one or more constant domains at the C-terminus. The constant domain of the light chain ($C_L$ which is ~110 amino acids in length) is aligned with and disulfide bonded to the first constant domain of the heavy chain ($C_H$ which is –330-440 amino acids in length). The light chain variable region is aligned with the variable region of the heavy chain. The antibody heavy chain can comprise 2 or more additional $C_H$ domains (such as, $C_H2$, $C_H3$ and the like) and can comprise a hinge region can be identified between the $C_H1$ and Cm constant domains. Antibodies can be of any type (e.g., IgG, IgE, IgM, IgD, IgA, and IgY), class (e.g., $IgG_1$, $IgG_2$, $IgG_3$, $IgG_4$, $IgA_1$ and $IgA_2$) or subclass. In one example, the antibody is a murine (mouse or rat) antibody or a primate (preferably human) antibody. The term "antibody" encompasses not only intact polyclonal or monoclonal antibodies, but also variants, fusion proteins comprising an antibody portion with an antigen binding site, humanised antibodies, human antibodies, chimeric antibodies, primatised antibodies, de-immunised antibodies or veneered antibodies.

The term "antigen binding fragment" shall be taken to mean any fragment of an antibody that retains the ability to bind to TnTuORF and preferably one which specifically binds to TnTuORF. This term includes a Fab fragment, a Fab' fragment, a F(ab') fragment, a single chain antibody (SCA or SCAB) amongst others. An "Fab fragment" consists of a monovalent antigen-binding fragment of an antibody molecule, and can be produced by digestion of a whole antibody molecule with the enzyme papain, to yield a fragment consisting of an intact light chain and a portion of a heavy chain. An "Fab' fragment" of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner. An "F(ab')2 fragment" of an antibody consists of a dimer of two Fab' fragments held together by two disulfide bonds, and is obtained by treating a whole antibody molecule with the enzyme pepsin, without subsequent reduction. An "Fv fragment" is a genetically engineered fragment containing the variable region of a light chain and the variable region of a heavy chain expressed as two chains. A "single chain antibody" (SCA) is a genetically engineered single chain molecule containing the variable region of a light chain and the variable region of a heavy chain, linked by a suitable, flexible polypeptide linker.

The term "'chimeric antibody" refers to antibodies in which a portion of the heavy and/or light chain is identical with or homologous to corresponding sequences in antibodies derived from a particular species (e.g., murine, such as mouse) or belonging to a particular antibody class or subclass, while the remainder of the chain(s) is identical with or homologous to corresponding sequences in antibodies derived from another species (e.g., primate, such as human) or belonging to another antibody class or subclass, as well as fragments of such antibodies, so long as they exhibit the desired biological activity (U.S. Pat. No. 4,816,567; and Morrison et al. (1984) *Proc. Natl Acad. Sci USA* 81:6851-6855).

The term "humanized antibody" shall be understood to refer to a chimeric molecule, generally prepared using recombinant techniques, having an epitope binding site derived from an immunoglobulin from a non-human species and the remaining immunoglobulin structure of the molecule based upon the structure and/or sequence of a human immunoglobulin. The antigen-binding site preferably comprises the complementarity determining regions (CDRs) from the non-human antibody grafted onto appropriate framework regions in the variable domains of human antibodies and the remaining regions from a human antibody. Epitope binding sites may be wild type or modified by one or more amino acid substitutions. It is known that the variable regions of both heavy and light chains contain three complementarity-determining regions (CDRs) which vary in response to the epitopes in question and determine binding capability, flanked by four framework regions (FRs) which are relatively conserved in a given species and which putatively provide a scaffolding for the CDRs. When non-human antibodies are prepared with respect to a particular epitope, the variable regions can be "reshaped" or "humanized" by grafting CDRs derived from nonhuman antibody on the FRs present in the human antibody to be modified.

The term "epitope" includes any antigenic (e.g., a protein) determinant capable of specific binding to an antibody and/or a T cell receptor. That is, a site on an antigen to which B and/or T cells respond. Epitopic determinants usually consist of chemically active surface groupings of molecules such as amino acids or sugar side chains, and usually have specific three-dimensional structural characteristics, as well as specific charge characteristics. An epitope typically includes, for example, at least 3, 5 or 8-10 amino acids. The amino acids may be contiguous, or non-contiguous amino acids juxtaposed by tertiary folding. Conformational and non-conformational epitopes are distinguished in that the binding to the former but not the latter is lost in the presence of denaturing solvents.

As used herein, the term "antigenic variant" refers to polypeptide sequences different from the specifically identified sequences, wherein one or more amino acid residues are deleted, substituted, or added. Substitutions, additions or deletions of 1, 2, 3 or 4 amino acids are specifically contemplated. Variants may be naturally-occurring allelic antigenic variants, or non-naturally occurring antigenic variants. Variants may be from the same or from other species and may encompass homologues, paralogues and orthologues. In certain embodiments, antigenic variants of the polypeptides useful in the invention have biological activities including hormone function or antigenic-binding properties that are the same or similar to those of the parent polypeptides. The term "antigenic variant" with reference to (poly)peptides encompasses all forms of polypeptides as defined herein. The term "antigenic variant" encompasses naturally occurring, recombinantly and synthetically produced polypeptides.

In addition to computer/database methods known in the art, polypeptide antigenic variants may be identified by physical methods known in the art, for example, by screening expression libraries using antibodies raised against polypeptides of the invention (Sambrook et al., Molecular Cloning: A Laboratory Manual, 2nd Ed. Cold Spring Harbor Press, 1987) by recombinant DNA techniques also described by Sambrook et al. or by identifying polypeptides from natural sources with the aid of such antibodies.

DETAILED DESCRIPTION

The use of Troponin T upstream open reading frame (TnTuORF) peptides and binding agents described herein in assays, methods and kits for the prognosis or diagnosis of cardiac disorders other than myocardial infarction or unstable angina are of clear clinical significance in detecting early onset of, for example, atrial fibrilation, heart failure, pericarditis, disorders of nerve conduction, vasovagalsyncope and combinations thereof (defined in Thygessen et al. (2012) *Circulation* 126:2020-2035; Table I on page 2024). The inventions described herein provide the clinician with the ability to stratify subjects who may be potentially at risk of a cardiac disorder or worsening of an existing cardiac disorder. Additionally, the methods, assays and kits of the present disclosure provide the clinician with a means to monitor a subject's responsiveness to existing therapy. For example, by measuring the TnTuORF levels in a subject over time, the clinician can monitor a subject's response to therapy or treatment.

Further, the present invention is drawn to assays, methods and kits involving binding agents specific for TnTuORF peptides for improving the sensitivity and false positive performance of cardiac troponins in predicting or diagnosing myocardial infarction, for improving the sensitivity and false positive performance of NT-proBNP in predicting a subject's risk of hospital readmission with acute decompensated heart failure following a cardiac event, and in predicting the mortality of a subject following a cardiac event.

The inventions described herein will become apparent having regard to the following detailed description.

TnTuORF Peptide is Present in Human Circulation

Applicants initially sought to confirm their hypothesis that a peptide encoded for by an upstream open reading frame of a cardiac troponin exists as a distinct and discrete biomarker in circulation, and in particular in human plasma.

Following detailed bioinformatic analysis of the cardiac troponin genes, Applicants identified an open reading frame (ORF) located −1512 by (i.e. upstream) of the major initiating codon for cardiac Troponin T (FIG. 1). With a Kozak score of +2 and high likelihood of being translated, Applicants predicted that this upstream open reading frame (uORF) should encode a putative 12 amino acid peptide and sought to confirm its existence using immunohistochemistry.

Applicants initially raised a polyclonal antibody directed toward the amino terminus of the putative 12 amino acid peptide with a predicted sequence of MAPEGWVIVVIS (SEQ ID NO:1). This antibody (r244) displayed little or no cross-reactivity to other known and established circulating peptides and/or drugs, and importantly including, for example, Cardiac Troponin T and Cardiac Troponin I, N-terminal brain natriuretic peptide (NT-proBNP) and the mature form of brain natriuretic peptide (BNP; Table III in Example 2).

Figure 2:
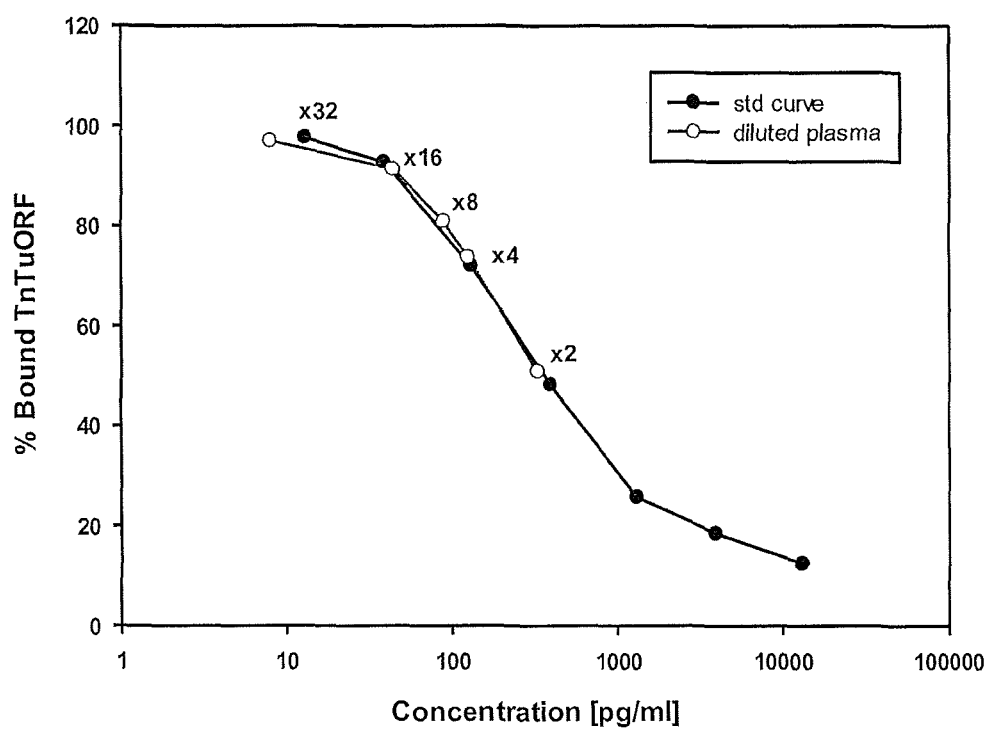
FIG. 2 shows representative TnTuORF immunoassay curve showing parallel dilution of human venous plasma (open circles; dilutions shown) compared with synthetic TnTuORF peptide standard curve (closed circles).

The r244 polyclonal antibody was then used to develop a sensitive and specific radioimmunoassay. FIG. 2 shows a representative TnTuORF immunoassay curve indicating parallel dilution of human venous plasma (obtained from peripheral blood of healthy adult subjects) compared to the synthetic TnTuORF peptide standard curve. These data provide the first direct evidence to demonstrate the existence of a peptide, encoded for by an upstream open reading frame coding sequence, in this case a uORF of Troponin T, which exists as a distinct chemical entity in circulation.

Further, and importantly, TnTuORF had no significant association with high sensitivity Troponin T (hsTnT) levels, age, blood pressure and body mass index.

Figure 5:
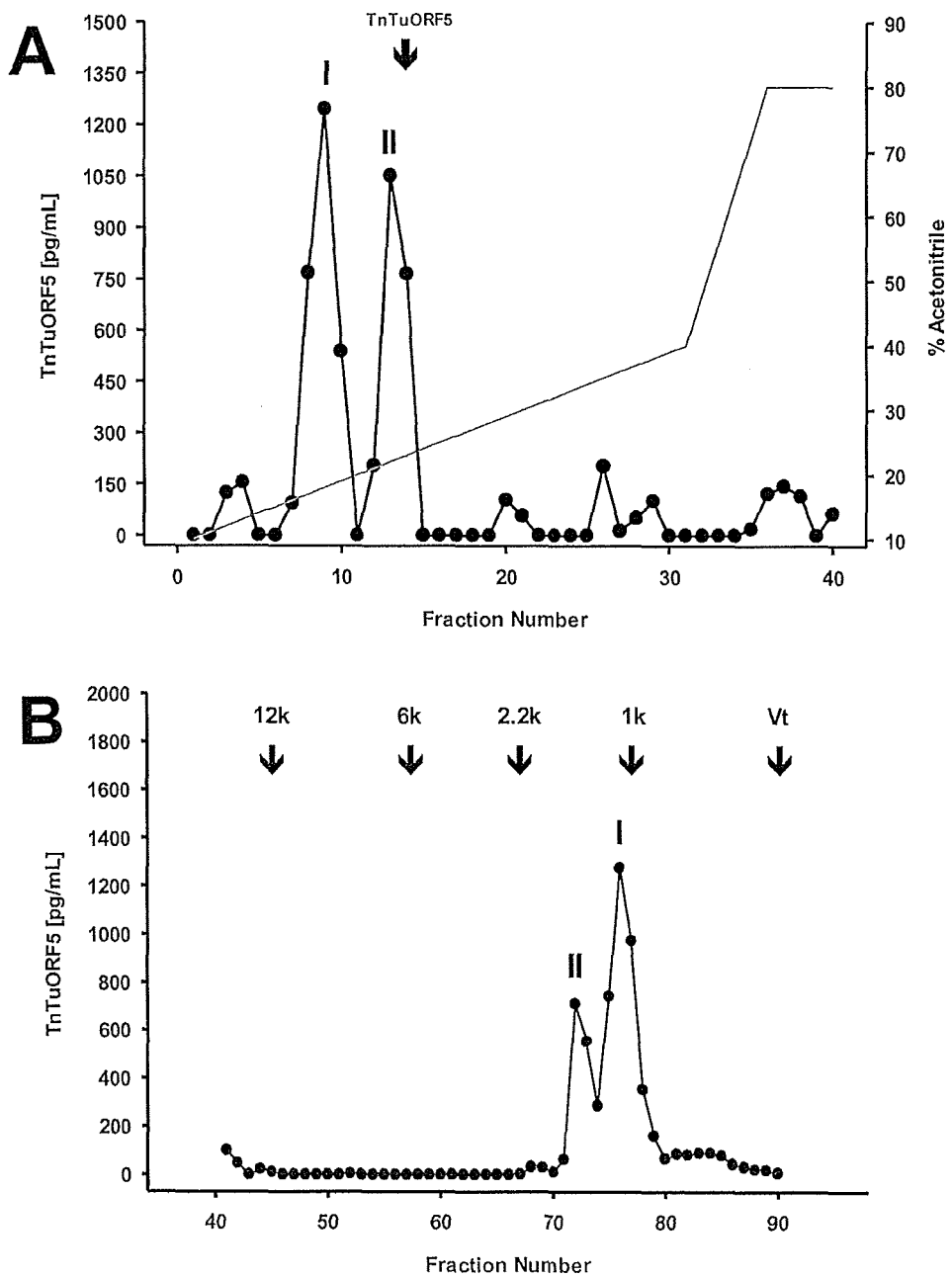
FIG. 5 shows high performance liquid chromatography (HPLC) of immunoreactive TnTuORF in the human circulation. (A) Immunoaffinity purified TnTuORF from human plasma eluted as two peaks (I and II) on reverse phase HPLC. Peak II eluted consistent with synthetic TnTuORF peptide as indicated. Grey line indicates concentration of acetonitrile. (B) Size exclusion HPLC of immunoreactive peaks I and II from panel A revealed peak II to have an apparent Mr of ~1.5 kilodalton (k), consistent with the theoretical weight of TnTuORF (predicted Mr 1.3 k). Peak I had an apparent Mr of ~1 k, consistent with a carboxyl terminus shortened form. Arrows indicate molecular weight values of calibration peptides. Vt=total volume of column.

Applicants next sought to identify the TnTuORF species detected by immunoassay through reverse phase high performance liquid chromatography (RP-HPLC) and size exclusion high performance liquid chromatography (SE-HPLC) coupled to immunoassay (FIG. 5). The results of these analyses confirmed that the immunoreactive TnTuORF is present in human plasma as (i) an in tact 12 amino acid peptide (i.e. MAPEGWVIVVIS; SEQ ID NO:1) and (ii) carboxy terminus shortened forms, including but not limited to MAPEGWVIVVI (SEQ ID NO: 2), MAPEGWVIVV (SEQ ID NO: 3) and MAPEGWVIV (SEQ ID NO:4).

TnTuORF as a Biomarker of Cardiac Disorders

Having established that immunoreactive TnTuORF is in fact present in human circulation, Applicants then sought to determine its potential clinical utility in cardiac disorders, including acute coronary syndromes. Initially, patients from four separate cohorts were recruited, namely, (i) healthy volunteers with no evidence or history of cardiovascular, endocrine or psychiatric illness (n=109), (ii) patients undergoing clinically indicated cardiac catheterisation (n=16), (iii) patients with documented ST-elevation myocardial infarction (n=4) and an acute coronary syndromes cohort (n=502). Details on the extent of blood sampling from these different patient cohorts are described in methods section in Example 1.

The initial set of measurements involved looking at potential clinical utility of circulating TnTuORF peptide as a diagnostic biomarker of acute cardiac ischemia resulting in myocardial infarction (i.e patient cohort (iii)). FIG. 5A shows that venous concentrations of TnTuORF peptide tended to decrease in the first 4-5 hours after symptom onset and although there was a general increase back to a plateau at about 24 hrs, the levels of TnTuORF were in fact less than half those observed in normal controls (Example 5). Compared with hsTnT, in which the concentration of this marker rises sharply in plasma of STEMI patients in the acute phase following an ischemic event (FIG. 5B), these data do not support the clinical utility of TnTuORF peptide in diagnosing acute cardiac ischemia resulting in myocardial infarction.

Figure 7:
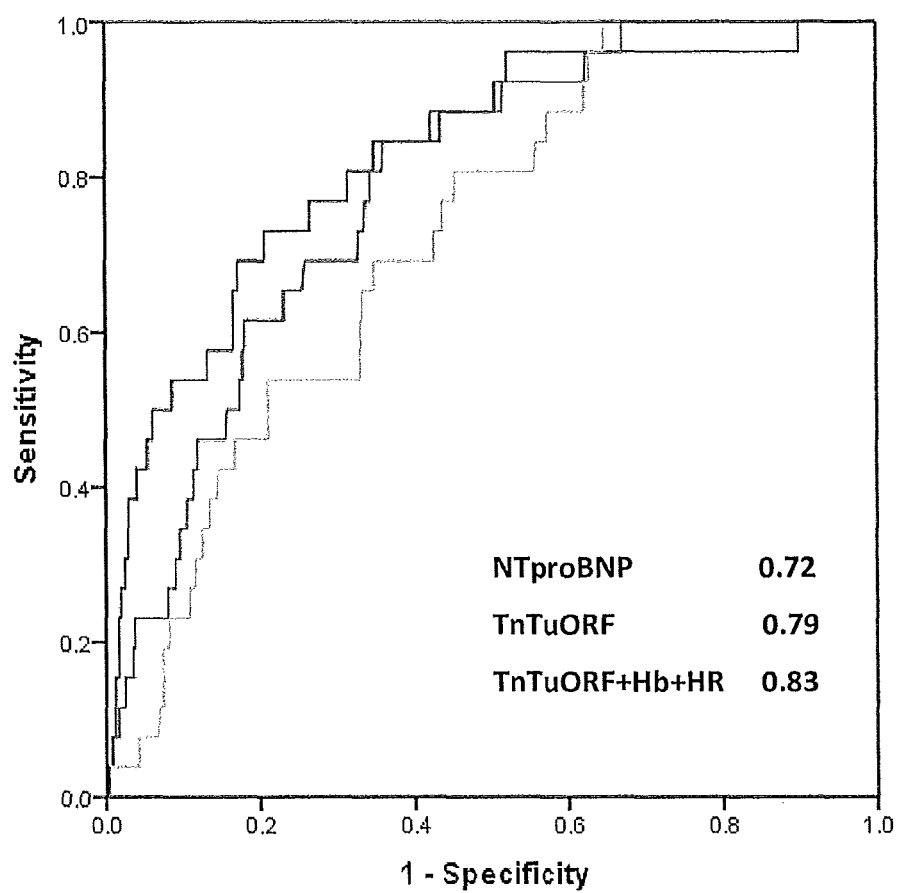
FIG. 7 shows receiver operator curve (ROC) analysis graphs of the performance of NTproBNP, TnTuORF and TnTuORF+Hb+Heart Rate (FIR) variables to diagnose other cardiac conditions (n=26).

To assess the potential utility of TnTuORF peptide in predicting or diagnosing other cardiac disorders, including acute coronary syndromes (Thygessen et al. (2012) *Circulation* 126:2020-2035), Applicants undertook a prospective, observational study of 502 patients presenting to the Emergency Department (ED) with the primary complaint of chest pain of suspected cardiac origin for which patient demographic and analyte data are presented in Table II (Example 1). The results of the various analyses confirmed that TnTuORF peptide plasma concentrations in patients presenting to ED had utility in the diagnosis of cardiac disorders other than myocardial infarction (MI) and unstable angina (UA; FIG. 7).

As such, Applicants have surprisingly found that in patients with a cardiac disorder other than myocardial infarction or unstable angina the circulating concentration of TnTuORF peptide is highest in the first twelve hours following the onset of the patient's symptoms. Levels observed in the first twelve, ten, eight, six, four, two or one hours of onset of, or at clinical presentation with the disorder hours were surprisingly high, often reaching up to 2-fold, 3-fold, 4-fold and 5-fold, and commonly 1.5-fold higher than levels in a normal control population.

In sum, one or more TnTuORF peptides is/are useful as clear early stage markers of, for example, cardiac disorders other than myocardial infarction or unstable angina, including, for example, atrial fibrillation, heart failure, pericarditis, disorders of nerve conduction and combinations thereof, as well as other disorders as noted herein.

Based on these surprising findings, Applicants have determined for the first time, that it would be useful to screen for one or more TnTuORF peptides or fragments thereof in a biological sample taken from a subject, particularly, for example, within twelve, ten, eight, six, four, two or one hours of onset of, or at clinical presentation with the disorder.

Accordingly, in one aspect of the present invention there is provided a method of predicting a subject's risk of acquiring a cardiac disorder other than myocardial infarction or unstable angina, the method comprising:
(i) measuring the level of a Troponin T upstream open reading frame (TnTuORF) peptide in a biological sample from the subject; and
(ii) comparing the measured level of the TnTuORF peptide against a reference interval from a suitable control population,
wherein an increase in the circulating level of the TnTuORF peptide compared with the control population is predictive of acquiring a cardiac disorder other than myocardial infarction or unstable angina, and further wherein the measuring step comprises detecting binding between the TnTuORF peptide and a binding agent that selectively binds to the TnTuORF peptide.

In another aspect of the present invention there is provided a method of diagnosing a cardiac disorder other than myocardial infarction or unstable angina in a subject, the method comprising:
(i) measuring the level of a Troponin T upstream open reading frame (TnTuORF) peptide in a biological sample from the subject; and
(ii) comparing the measured level of the TnTuORF peptide against a reference interval from a suitable control population,
wherein an increase in the circulating level of the TnTuORF peptide compared with the control population is indicative of a cardiac disorder other than myocardial infarction or unstable angina, and further wherein the measuring step comprises detecting binding between the TnTuORF peptide and a binding agent that selectively binds to the TnTuORF peptide.

The skilled reader will appreciate that for evaluation purposes, the level of TnTuORF peptide may usefully be compared or correlated with a reference value or control value. In one embodiment the control population is sex and age-matched subjects for which the cardiac disorder is known.

As used herein a control population can be an individual or group from which samples of a TnTuORF peptide are taken and a mean level determined. Usually, the individual or group will comprise normal healthy individuals or a group of individuals not known to be suffering from a cardiac disorder. In one embodiment, the reference interval is the mean circulating TnTuORF peptide concentration from the control population. Levels of TnTuORF peptides in control populations range from between about 430-1130 pg/mL, with a mean of about 778 pg/mL ($P<0.001$)). Alternatively, the control population may be assessed based on a plurality of readings from previously tested individuals or groups. Levels in the order of 730-1590 pg/mL, with a mean of about 1159 pg/mL are typically indicative of a cardiac disorder other than myocardial infarction or unstable angina.

It will be appreciated that the step of measuring levels of TnTuORF peptides in a sample may be a single measurement on a single sample, or repeated measurements on a number of samples depending on the biological event being studied. In the case of a cardiac disorder, measurement may comprise, for example, 1 to 20 or more measurements of TnTuORF peptide, 1 to 10, 1 to 5, 1 to 3, or 2 or 3 measurements of a TnTuORF peptide in samples taken at different times. In one embodiment the measurements are on samples taken within the first twelve, ten, eight, six, five, four, two hours, or within one hour or less of, onset of or clinical presentation with a disorder or suspected disorder. Single, or repeated measurements outside the sample period above may also be taken to establish whether the level of a TnTuORF peptide has fallen to the normal control level, or, for example, cardiac tissue control level.

The assays, methods and kits of the present invention comprise measuring levels of a TnTuORF peptide in one or two samples taken within the first hour of onset or presentation, followed by measuring levels of a TnTuORF peptide in one or two samples taken within two to four hours, or two to three hours of onset or presentation, or initial measurement of the level of a TnTuORF peptide.

Accordingly, in certain embodiments, the method of predicting a subject's risk of acquiring a cardiac disorder other than myocardial infarction or unstable angina or the method of diagnosing a cardiac disorder other than myocardial infarction or unstable angina in a subject further comprises measuring the level of the TnTuORF peptide in a first biological sample from the subject and measuring the level of the TnTuORF peptide in a second biological sample, wherein the second biological sample is taken from the same subject as the first biological sample but at a later period in time, and comparing the levels of TnTuORF peptide in the first and second samples, wherein an increase in the circulating level of TnTuORF peptide between the first and second samples is indicative of increased risk to acquiring the cardiac disorder.

As noted above, levels of a TnTuORF peptide may be measured within the first one to twelve, ten, eight, six, four or two hours or less of onset or presentation of a cardiac disorder and are, for example, 1.5-5-fold higher than levels measured in a normal control.

The biological sample as defined above can be any biological material in which a TnTuORF peptide can be located or secreted. In one embodiment a biological sample is a circulatory biological sample, for example venous blood and arterial blood, plasma, serum or interstitial fluid. In another embodiment, the biological sample is cardiac tissue or heart tissue sample.

The term "measuring the level of a TnTuORF peptide" in a biological sample refers to methodologies that enable the determination of TnTuORF peptide level or concentration in the sample, such as, for example an immunoassay including radioimmunoassay, enzyme linked immunosorbent assay (ELISA), immunofluorometric assay and immunoradiometric assay, as will be known to a person skilled in the art. In one example, the TnTuORF peptide level is expressed as pg/mL. The terms TnTuORF peptide level and TnTuORF peptide concentration may be used interchangeably.

In the assays, methods and kits according to the present invention, the measuring steps comprise detecting binding between a TnTuORF peptide and a binding agent that binds, selectively or specifically, to the TnTuORF peptide, and has low cross-reactivity with other markers of biological events. In certain embodiments, the binding agent is an antibody or an antigen-binding fragment thereof. The antibody may be a monoclonal, polyclonal, chimeric or humanized antibody or antigen-binding fragment thereof. In other embodiments, the binding agent or antibody may be immobilised to a solid phase. A more detailed description of binding agents, including antibodies and antigen-binding fragments, is outlined elsewhere in this specification.

The specificity and sensitivity of TnTuORF peptide in predicting or diagnosing cardiac disorders other than myocardial infarction or unstable angina was further improved when the concentration of TnTuORF was added to heart rate values and heamoglobin concentration. By way of illustration, and in reference to FIG. 7, when TnTuORF was added to heart rate and Hb concentration, the diagnosis of cardiac disorders other than myocardial infarction and unstable angina improved from AUC=0.79 (P<0.001) to AUC 0.83 (P<0.001). Accordingly, in certain embodiments of the present invention, the assays, methods and kits for predicting or diagnosing a cardiac disorder of the present invention may also be performed in conjunction with the analysis of one or more risk factors such as, for example, heart rate, haemoglobin concentration, blood pressure, age, sex, weight, level of physical activity, family history of events including obesity, diabetes and cardiac events, and circulating levels of Troponin T and Troponin I.

With respect to the "AUC" values referred to above, and as described in the Examples which follow with regard to TnTuORF peptides and their ability to predict or diagnose a subject with a cardiac disorder, population studies may also be used to select a decision threshold. Receiver Operating Characteristic ("ROC") arose from the field of signal dectection theory developed during World War H for the analysis of radar images, and ROC analysis is often used to select a threshold able to best distinguish a "diseased" subpopulation from a "nondiseased" subpopulation. A false positive in this case occurs when the person tests positive, but actually does not have the disease. A false negative, on the other hand, occurs when the person tests negative, suggesting they are healthy, when they actually do have the disease. To draw a ROC curve, the true positive rate (TPR) and false positive rate (FPR) are determined as the decision threshold is varied continuously. Since TPR is equivalent with sensitivity and FPR is equal to 1-specificity, the ROC graph is sometimes called the sensitivity vs (1-specificity) plot. A perfect test will have an area under the (ROC) curve (i.e. AUC) of 1.0; a random test will have an area of 0.5. A threshold is selected to provide an acceptable level of specificity and sensitivity.

As described above, the methods, assays and kits of the present disclosure provide the clinician with a means to monitor a subject's responsiveness to existing therapy.

Accordingly, in another embodiment of the present invention, the methods for predicting or diagnosing a subject with a cardiac disorder other than myocardial infarction or unstable angina further comprise administering a treatment regimen to the subject where the subject is found to have an increase in a circulating level of the TnTuORF peptide compared with the circulating level of the TnTuORF peptide in the control population.

Further, in yet another aspect of the present invention there is provided for monitoring the responsiveness of a subject to treatment with a drug or therapy for a cardiac disorder other than myocardial infarction or unstable angina, the method comprising:
(i) measuring the level of TnTuORF in a first biological sample from the subject;
(ii) measuring the level of TnTuORF in a second biological sample from the subject, wherein the second biological sample is taken from the same subject; and
(iii) comparing the measured levels of TnTuORF in the first and second samples,
wherein an increase in the level of TnTuORF between the first and second samples is indicative of a poor response to treatment with a with a drug or therapy for a cardiac disorder other than myocardial infarction or unstable angina and wherein a decrease in the level of TnTuORF between the first and second samples is indicative of a positive response to a to treatment with a with a drug or therapy for a cardiac disorder other than myocardial infarction or unstable angina.

Contingent on the cardiac disorder to be treated, it is possible that an increased level of TnTuORF peptide between the first and second samples is indicative of a positive response to treatment with a drug or therapy for a cardiac disorder other than myocardial infarction or unstable angina. Put another way, a decreased level of TnTuORF peptide between the first and second samples is indicative of a poor response to treatment with a drug or therapy for a cardiac disorder other than myocardial infarction or unstable angina.

Accordingly, in yet a further aspect of the present invention there is provided a method for monitoring the responsiveness of a subject to treatment with a drug or therapy for a cardiac disorder other than myocardial infarction or unstable angina, the method comprising:
(i) measuring the level of a TnTuORF peptide in a first biological sample from the subject;
(ii) measuring the level of a TnTuORF peptide in a second biological sample from the subject, wherein the second biological sample is taken from the same subject; and
(iii) comparing the measured levels of the TnTuORF peptide in the first and second samples,
wherein a decrease in the level of TnTuORF peptide between the first and second samples is indicative of a poor response to treatment with a with a drug or therapy for a cardiac disorder other than myocardial infarction or unstable angina and wherein an increase in the level of TnTuORF peptide between the first and second samples is indicative of a positive response to a to treatment with a with a drug or therapy for a cardiac disorder other than myocardial infarction or unstable angina.

Where a subject is to be monitored, a number of biological samples may be taken over time. Serial sampling allows changes in marker levels to be measured over time. Sampling can provide information on the approximate onset time of an event, the severity of the event, indicate which therapeutic regimes may be appropriate, response to therapeutic regimes employed, or long term prognosis. Analysis may be carried out at points of care such as in ambulances, doctors' offices, on clinical presentation, during hospital stays, in outpatients, or during routine health screening, etc.

Again, the method may also be performed in conjunction with the analysis of one or more risk factors of cardiac disorders such as, for example, heart rate, haemoglobin concentration, blood pressure, age, sex, weight, level of physical activity, family history of events including obesity, diabetes and cardiac events, and circulating levels of Troponin T and Troponin I.

Finally, a person skilled in the art will appreciate that the present invention is also directed to the specific TnTuORF peptide binding members, as well as their use in the manufacture of medicaments for predicting or diagnosing a subject with, or at risk of developing, a cardiac disorder other than myocardial infarction or unstable angina.

Accordingly, the present invention also provides a Troponin T upstream open reading frame (TnTuORF) peptide binding agent that selectively binds TnTuORF peptide for use in predicting a subject's risk of acquiring a cardiac disorder other than myocardial infarction or unstable angina.

The present invention further provides a Troponin T upstream open reading frame (TnTuORF) peptide binding agent that selectively binds TnTuORF peptide for use in diagnosing a cardiac disorder other than myocardial infarction or unstable angina in a subject.

The present invention also provides a use of a Troponin T upstream open reading frame (TnTuORF) peptide binding agent that selectively binds to a TnTuORF peptide in the manufacture of a medicament for predicting a subject's risk for acquiring a cardiac disorder other than myocardial infarction or unstable angina.

The present invention further provides a use of a Troponin T upstream open reading frame (TnTuORF) peptide binding agent that selectively binds to a TnTuORF peptide in the manufacture of a medicament for diagnosing a cardiac disorder other than myocardial infarction or unstable angina in a subject.

TnTuORF as a Biomarker of Myocardial Infarction

Figure 8:
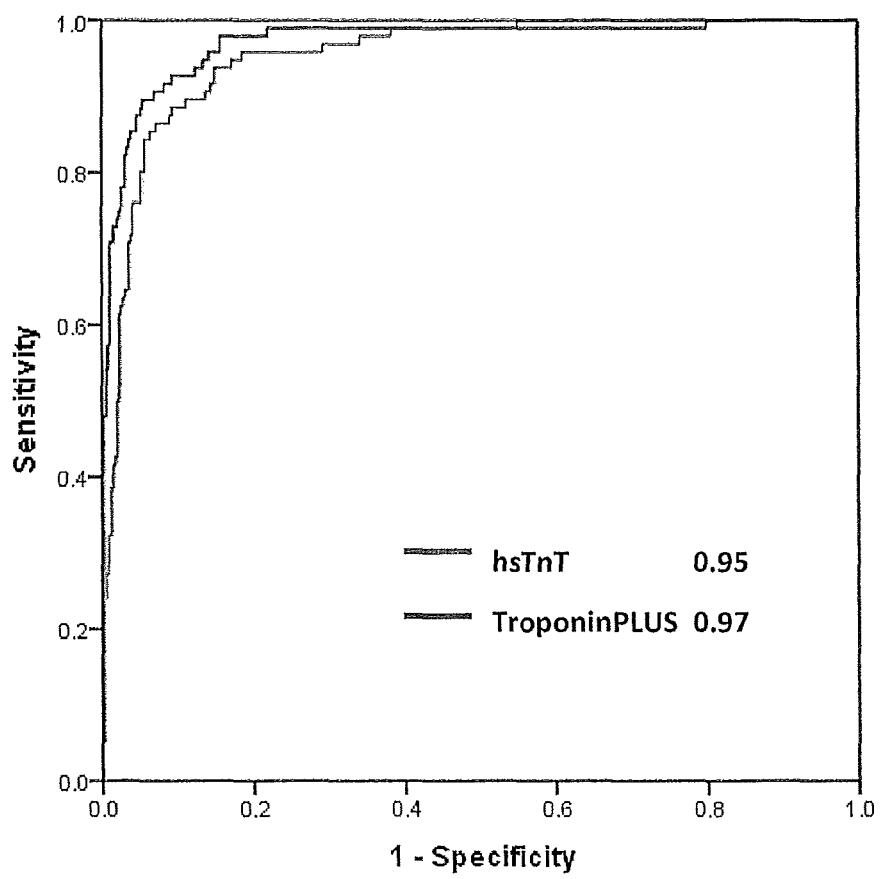
FIG. 8 shows receiver operator curve (ROC) analysis graphs of the performance of hsTnT and Troponin PLUS to diagnose acute NSTEMI (n=96).

Despite its lack of utility in being able to directly predict or diagnose acute cardiac ischemia resulting in myocardial infarction, surprisingly, Applicants demonstrate that TnTuORF peptide improves the sensitivity and false positive performance of existing cardiac troponin biomarkers in predicting and/or diagnosing myocardial infarction. In absolute terms, the product ratio of Troponin I×hsTroponin T/TnTuORF (herein referred to as TroponinPLUS™) increased by 4% the number of myocardial infarction patients detected within 2 hours (i.e. 94/96 NSTEMI patients or 98%; compared with hsTnT which detected 90/96 NSTEMI patients or 90% and TnI which detected 88/96 NSTEMI patients or 92%) and reduced the false positive diagnosis rate by 7% (Example 6; FIG. 8).

Accordingly, in a further aspect of the present invention there is provided an assay for improving the sensitivity and false positive performance of cardiac troponin in predicting a subject's risk of myocardial infarction, the assay comprising a binding agent that selectively binds to a Troponin T upstream open reading frame (TnTuORF) peptide and which binding agent can be quantatively measured upon binding to the TnTuORF peptide in a biological sample from the subject.

The invention further provides an assay for improving the sensitivity and false positive performance of cardiac troponin in diagnosing myocardial infarction in a subject, the assay comprising a binding agent that selectively binds to a Troponin T upstream open reading frame (TnTuORF) peptide and which binding agent can be quantatively measured upon binding to the TnTuORF peptide in a biological sample from the subject.

In one embodiment according to either aspect, the cardiac troponin comprises Troponin T and Troponin I. In an example, the cardiac troponin can be represented by highly sensitivity Troponin T (hsTnT)×Troponin I. In another embodiment, the sensitivity and false positive performance of cardiac troponin is improved by taking the product ratio of cardiac troponin to TnTuORF peptide. In an example the product ratio is represented by hsTnT×TnI/TnTuORF. As described above, this product ratio increases the sensitivity and false positive performance of cardiac troponin in predicting or diagnosing myocardial infarction.

The present invention also provides a kit for measuring the level of a Troponin T upstream open reading frame (TnTuORF) peptide in a biological sample from a subject for use in improving the sensitivity and false positive performance of cardiac troponin in predicting or diagnosing myocardial infarction in the subject, the kit comprising a binding agent that selectively binds to a TnTuORF peptide and which binding agent can be quantatively measured upon binding to TnTuORF.

In one embodiment, the kit further comprises instructions for how to measure the level of TnTuORF peptide.

The present invention further provides a Troponin T upstream open reading frame (TnTuORF) peptide binding agent that selectively binds to a TnTuORF peptide in a biological sample from a subject for use in improving the sensitivity and false positive performance of cardiac troponin in predicting or diagnosing myocardial infarction in the subject.

Furthermore, with respect to prognosis, TroponinPLUS™ (i.e. hsTnT×TnI/TnTuORF) predicted mortality at 1 year (AUC=0.74, P<0.001), more accurately than hsTnT and TnI alone (AUC=0.72 and 0.71, respectively) but did not improve on either Troponin T or Troponin I to predict readmission with myocardial infarction or chronic heart failure within one year.

Accordingly, in yet a further aspect of the present invention there is provided an assay for predicting mortality in a subject following a cardiac event, the assay comprising a binding agent that selectively binds to a Troponin T upstream open reading frame (TnTuORF) peptide and which binding agent can be quantatively measured upon binding to the TnTuORF peptide in a biological sample from the subject.

In one embodiment, the assay can be used to predict mortality in the subject up to 9 months, 10 months, 11 months, 12 months, 13 months, 14 months and 15 months following the cardiac event, and more commonly 12 months following the cardiac event.

The present invention further provides a Troponin T upstream open reading frame (TnTuORF) peptide binding agent that selectively binds to a TnTuORF peptide in a biological sample from a subject for use in predicting mortality of the subject following a cardiac event.

Figure 9:
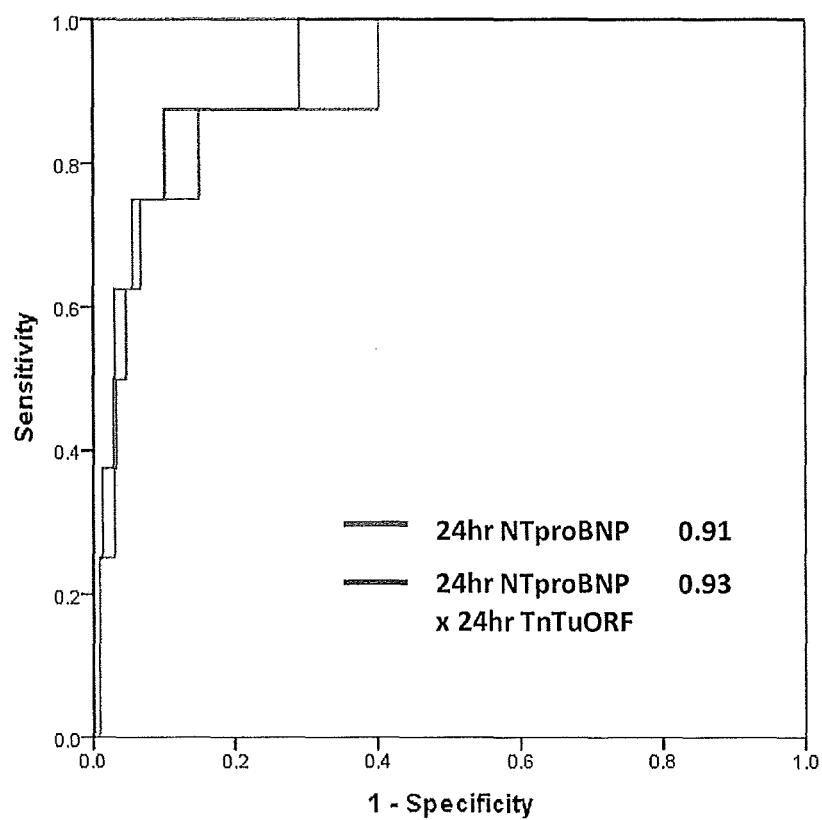
FIG. 9 shows receiver operator curve (ROC) analysis graphs showing the prognostic ability of 24 hour NTproBNP and NTproBNPxTnTuORF to predict readmission with acute decompensated heart failure within one year of index admission (n=10).

Addition of single inpatient 24 hour TnTuORF concentration to matched NTproBNP improved the ROC curve for 24 hour NTproBNP alone to predict readmission with acute decompensated heart failure (ADHF) around one year (AUC=0.93 vs. 0.91; FIG. 9).

Accordingly, in a further aspect of the present invention there is provided an assay for improving the sensitivity and false positive performance of N-terminal brain natriuretic peptide (NT-proBNP) in predicting a subject's risk of acquiring acute decompensated heart failure following a cardiac event, the assay comprising a binding agent that selectively binds to a Troponin T upstream open reading frame (TnTuORF) peptide and which binding agent can be quantatively measured upon binding to the TnTuORF peptide in a biological sample from the subject.

In one embodiment, the assay can be used to predict a subject's risk of acquiring acute decompensated heart failure following a cardiac event up to 9 months, 10 months, 11 months, 12 months, 13 months, 14 months and 15 months following the cardiac event, and more commonly 12 months following the cardiac event The present invention further provides a kit for measuring the level of a Troponin T upstream open reading frame (TnTuORF) peptide in a biological sample from a subject for use in improving the sensitivity and false positive performance of N-terminal brain natriuretic peptide (NT-proBNP) in predicting the subject's risk of acquiring acute decompensated heart failure following a cardiac event, the kit comprising a binding agent that selectively binds to a TnTuORF peptide and which binding agent can be quantatively measured upon binding to TnTuORF.

Finally, the present invention also provides a Troponin T upstream open reading frame (TnTuORF) peptide binding agent that selectively binds to a TnTuORF peptide in a biological sample from a subject for use in improving the sensitivity and false positive performance of N-terminal brain natriuretic peptide (NT-proBNP) in predicting the subject's risk of acquiring acute decompensated heart failure following a cardiac event.

Binding Agents to TnTuORF

TnTuORF peptides are measured in a body fluid sample by detecting binding between a TnTuORF peptide and a binding agent that selectively binds to the TnTuORF peptide. Binding agents for use in the methods of the present disclosure preferably have low cross-reactivity, for example with ANP and BNP. The binding agents may include antibodies or antigen-binding fragments such as Fab and F(ab)$_2$, prepared using antigenic TnTuORF peptides or fragments thereof as immunising antigens. The polypeptide or fragments may also be coupled to a carrier as described. In one example, the binding agent is an antibody. The antibody may be a monoclonal or polyclonal antibody. Methods for producing polyclonal and monoclonal antibodies as well as fragments thereof are well known in the art (for example see Harlow and Lane, Antibodies: A Laboratory Manual, Cold Spring Harbor Laboratory, New York 1988), but have also been developed in-house by Applicants (e.g. Siriwardena et al. (2010) *Circulation* 122:255-264). For reasons of specificity, monoclonal antibodies are preferred. It will be appreciated by a person skilled in the art that humanised antibodies are not required for in vitro assays.

In one example, the antibody is raised against an antigenic TnTuORF peptide. In one example, the antigenic TnTuORF peptide comprises MAPEGWVIVVIS (SEQ ID NO: 1), MAPEGWVIVVI (SEQ ID NO: 2), MAPEGWVIVV (SEQ ID NO: 3) or MAPEGWVIV (SEQ ID NO: 4), This generally provides a sufficient epitope for specific amino acid detection.

Monoclonal antibodies may be produced by known art methods. These include the immunological method described by Kohler et al (1975) Nature 256(5517):495-7 as well as the recombination DNA method described by Huse et at (1989) 246(4935):1275-81. The use of recombinant phage antibody systems to produce single chain variable antibody fragments, and subsequent mutation (such as site specific mutagenesis) or chain shifting to produce antibodies to NT-CNP peptides is also contemplated.

Conventional procedures for generating polyclonal antibodies are detailed in Harlow and Lane (supra). Briefly, the protocol requires immunisation of a selected animal host such as a rabbit, goat, donkey, sheep, rat or mouse (usually a rabbit), with an isolated NT-CNP peptide on a number of spaced occasions, with one or more test bleeds preceding exsanguination and blood collection. Serum may be separated from clotted blood by centrifugation. Serum may be tested for the presence of polyclonal antibodies using ELISA or radioimmunoassay competitive assays or art equivalent methods.

Antibodies specific to TnTuORF can be raised after first conjugating these or similar peptides to a large protein such as limpet hemocyanin (KLH), bovine serum albumin (BSA) or bovine thyroglobulin to make them immunogenic. Coupling can be effected by use of any protein crosslinking agent including for example the common agents glutaraldehyde, carbodiimide or N-(e-maleimido-caproyloxy) succinimide ester (MCS)—providing a cysteine residue is added to the peptide sequence prior to coupling. Injection of these conjugates into rabbits, sheep, mice or other species at monthly intervals followed by collection of blood samples two weeks later will enable production of polyclonal antibodies or monoclonal antibodies from the spleens of mice.

For example, the mouse host described above may be sacrificed and its spleen removed. The messenger RNA (mRNA) are then isolated and cDNA made from the mRNA using specific primers for the heavy and light chains of the variable region of the antibodies and the polymerase chain reaction (PCR) amplification. The DNA sequences for the heavy and light chains are joined with a linker sequence, to ensure the correct reading frame. Then the DNA construct is inserted into a vector, for example, a plasmid or bacteriophage, or virus, for transformation into a host. In one example the vector is a bacteriophage.

Suitable hosts may be selected from prokaryotic, yeast, insect or mammalian cells. In one example, a prokaryotic host, preferably *Escherichia coli* is used. The bacteriophage produces a viral coat and the antibody fragments are expressed on the coat, a phage display library. The phage display library can be screened for antibody fragments with the appropriate affinity for the specific antigens. The library can be screened many times and modifications can be made to the antibody construct through protein engineering techniques, such as site directed mutagenesis and chain shuffling all of which are within the capabilities of the person skilled in the art.

Detection of Binding Agents Including Peptide Binding Assays

The present invention includes use of a detection system involving the binding of TnTuORF peptides to a binding agent and then detecting the amount of bound peptide. A similar solution is to detect the amount of unbound binding agent in a sample to get an indication of unbound or bound TnTuORF. It is intended that such alternative methods fall within the scope of the present invention as functional alternatives to directly detecting the amount of bound binding agent. Persons skilled in the art will appreciate that the concentration of TnTuORF in a sample can be readily calculated from the amount of TnTuORF in a sample when the sample volume is known.

In the assays, methods and kits according to the present invention, the measuring steps comprise detecting binding between a TnTuORF peptide and a binding agent that binds, selectively or specifically, to the TnTuORF peptide, and has low cross-reactivity with other markers of biological events.

Accordingly, in yet another aspect of the present invention there is provided an assay for measuring the level of a Troponin T upstream open reading frame (TnTuORF) peptide in a biological sample from a subject with, or at risk of acquiring, a cardiac disorder other than myocardial infarction or unstable angina, comprising a binding agent that selectively binds to a TnTuORF peptide and which binding agent can be quantatively measured upon binding to the TnTuORF peptide.

In certain embodiments, the binding agent is an antibody or an antigen-binding fragment thereof. The antibody may be a monoclonal, polyclonal, chimeric or humanized antibody or antigen-binding fragment thereof. As such, in one embodiment the assay of the present invention is an immunoassay.

The antibodies of the present invention are particularly useful in immunoassays for determining the presence and/or amount of TnTuORF in a sample. Due to variable binding affinities of different antibodies, the person skilled in the art will appreciate that a standard binding curve of measured values versus amount of TnTuORF in a sample should be established for a particular antibody to enable the amount of TnTuORF in a sample to be determined. Such a curve is used to determine the true amount of TnTuORF in a sample.

Sample materials include biological fluids but are not limited thereto. In terms of the present disclosure, usually a biological fluid is selected from whole blood, plasma or serum.

Immunoassays specific for TnTuORF peptides usually will require the production of antibodies that specifically bind to TnTuORF peptides. In one example, the antibody recognizes a TnTuORF peptide defined by MAPEGWVIV-VIS (SEQ ID NO:1), MAPEGWVIVVI (SEQ ID NO: 2), MAPEGWVIVV (SEQ ID NO: 3) or MAPEGWVIV (SEQ ID NO: 4). The antibodies can be used to construct immunoassays with broad specificity, as in competitive binding assays below, or used in conjunction with other antibodies described below in sandwich type assays to produce assays specific to TnTuORF peptides. The person skilled in the art will appreciate that non-competitive assays are also possible. The latter antibodies for sandwich immunoassays include those specific for amino acid sequences including MAPEGWVIVVIS (SEQ ID NO: 1) as well as carboxy shortened forms thereof (i.e. SEQ ID NOs: 2-4).

In another example, indicators may also be used Indicators may be employed in ELISA and RIA assay formats.

Polyclonal and monoclonal antibodies can be used in competitive binding or sandwich type assays. In one example of this method a liquid sample is contacted with the antibody and simultaneously or sequentially contacted with a labelled TnTuORF peptide or modified peptide containing the epitope recognised by the antibody.

The label can be a radioactive component such as $^{125}$I, $^{131}$I, $^{3}$H, $^{14}$C or a nonradioactive component that can be measured by time resolved fluorescence, fluorescence, fluorescence polarisation, luminescence, chemiluminescence or colorimetric methods. These compounds include europium or other actinide elements, acrinidium esters, fluorescein, or radioactive material such as those above, that can be directly measured by radioactive counting, measuring luminescent or fluorescent light output, light absorbance etc. The label can also be any component that can be indirectly measured such as biotin, digoxin, or enzymes such as horseradish peroxidase, alkaline phosphatase. These labels can be indirectly measured in a multitude of ways. Horseradish peroxidase for example can be incubated with substrates such as o-Phenylenediamine Dihyhdrochloride (OPD) and peroxide to generate a coloured product whose absorbance can be measured, or with luminol and peroxide to give chemiluminescent light which can be measured in a luminometer. Biotin or digoxin can be reacted with binding agents that bind strongly to them; e.g. avidin will bind strongly to biotin. These binding agents can in turn be covalently bound or linked to measurable labels such as horseradish peroxidase or other directly or indirectly measured labels as above. These labels and those above may be attached to the peptide or protein: during synthesis, by direct reaction with the label, or through the use of commonly available crosslinking agents such as MCS and carbodiimide, or by addition of chelating agents.

Following contact with the antibody, usually for 18 to 25 hours at 4° C., or 1 to 240 minutes at 30° C. to 40° C., the labelled peptide bound to the binding agent (antibody) is separated from the unbound labelled peptide. In solution phase assays, the separation may be accomplished by addition of an anti gamma globulin antibody (second-antibody) coupled to solid phase particles such as cellulose, or magnetic material. The second-antibody is raised in a different species to that used for the primary antibody and binds the primary antibody. All primary antibodies are therefore bound to the solid phase via the second antibody. This complex is removed from solution by centrifugation or magnetic attraction and the bound labelled peptide measured using the label bound to it. Other options for separating bound from free label include formation of immune complexes, which precipitate from solution, precipitation of the antibodies by polyethyleneglycol or binding free labelled peptide to charcoal and removal from solution by centrifugation of filtration. The label in the separated bound or free phase is measured by an appropriate method such as those presented above.

Competitive binding assays can also be configured as solid phase assays that are easier to perform and are therefore preferable to those above. This type of assay uses plates with wells (commonly known as ELISA or immunoassay plates), solid beads or the surfaces of tubes. The primary antibody is either adsorbed or covalently bound to the surface of the plate, bead or tube, or is bound indirectly through a second anti gamma globulin or anti Fc region antibody adsorbed or covalently bound to the plate. Sample and labelled peptide (as above) are added to the plate either together or sequentially and incubated under conditions allowing competition for antibody binding between TnTuORF in the sample and the labelled peptide. Unbound labelled peptide can subsequently be aspirated off and the plate rinsed leaving the antibody bound labelled peptide attached to the plate. The labelled peptide can then be measured using techniques described above.

Sandwich type assays are more preferred for reasons of specificity, speed and greater measuring range. In this type of assay an excess of the primary antibody to NT-CNP is attached to the well of an ELISA plate, bead or tube via adsorption, covalent coupling, or an anti Fc or gamma globulin antibody, as described above for solid phase competition binding assays. Sample fluid or extract is contacted with the antibody attached to the solid phase. Because the antibody is in excess this binding reaction is usually rapid. A second antibody to a TnTuORF peptide is also incubated with the sample either simultaneously or sequentially with the primary antibody. This second antibody is chosen to bind to a site on NT-CNP that is different from the binding site of the primary antibody. These two antibody reactions result in a sandwich with the NT-CNP from the sample sandwiched between the two antibodies. The second antibody is usually labelled with a readily measurable compound as detailed above for competitive binding assays. Alternatively a labelled third antibody which binds specifically to the second antibody may be contacted with the sample. After washing the unbound material the bound labelled antibody can be measured by methods outlined for competitive binding assays. After washing away the unbound labelled antibody, the bound label can be quantified as outlined for competitive binding assays.

A dipstick type assay may also be used. These assays are well known in the art. They may for example, employ small particles such as gold or coloured latex particles with specific antibodies attached. The liquid sample to be measured may be added to one end of a membrane or paper strip preloaded with the particles and allowed to migrate along the strip. Binding of the antigen in the sample to the particles modifies the ability of the particles to bind to trapping sites, which contain binding agents for the particles such as antigens or antibodies, further along the strip. Accumulation of the coloured particles at these sites results in colour development are dependent on the concentration of competing antigen in the sample. Other dipstick methods may employ antibodies covalently bound to paper or membrane strips to trap antigen in the sample. Subsequent reactions employing second antibodies coupled to enzymes such as horse radish peroxidase and incubation with substrates to produce colour, fluorescent or chemiluminescent light output will enable quantitation of antigen in the sample.

Kits

Typically, kits will be formatted for assays known in the art, and in certain embodiments for RIA or ELISA assays, as are known in the art.

The kits may also include one or more additional markers for the disorders noted herein. In the case of cardiac disorders, for example, the additional marker may include one or more of troponin T, troponin I, creatin kinase MB, myoglobin, ANP, BNP, BNP-SP, ANP, ANP-SP, NT-BNP, LDH, aspartate aminotransferase, H-FABP, endothelin, adrenomedullin, rennin and angiotensin II.

The kit may be comprised of one or more containers and may also include collection equipment, for example, bottles, bags (such as intravenous fluids bags), vials, syringes, and test tubes. A t least one container will be included and will hold a product which is effective for predicting, diagnosing, or monitoring a biological event such as a cardiac disorder other than myocardial infarction or unstable angina etc. The product is usually a polypeptide and/or a binding agent, particularly an antibody or antigen-binding fragment of the invention, or a composition comprising any of these. In one embodiment, an instruction or label on or associated with the container indicates that the composition is used for predicting, diagnosing, or monitoring the cardiac disorder. Other components may include needles, diluents and buffers. Usefully, the kit may include at least one container comprising a pharmaceutically acceptable buffer, such as phosphate-buffered saline, Ringer's solution or dextrose solution.

Binding agents that selectively bind TnTuORF peptides or fragment(s) thereof are desirably included in the kit. In one embodiment, the binding agent is an antibody or antigen-binding fragment of the invention. The antibody used in the assays and kits may be monoclonal or polyclonal, for example, and may be prepared in any mammal as described above, and includes antigen binding fragments and antibodies prepared using native and fusion peptides, for example.

In one kit embodiment a TnTuORF peptide binding agent is immobilized on a solid matrix, for example, a porous strip or chip to form at least one detection site for a TnTuORF peptide or a fragment(s) thereof. The measurement or detection region of the porous strip may include a plurality of detection sites, such detection sites containing a detection reagent. The sites may be arranged in a bar, cross or dot or other arrangement. A test strip or chip may also contain sites for negative and/or positive controls. The control sites may alternatively be on a different strip or chip. The different detection sites may contain different amounts of immobilized nucleic acids or antibodies, e.g., a higher amount in the first detection site and lower amounts in subsequent sites. Upon the addition of a test biological sample the number of sites displaying a detectable signal provides a quantitative indication of the amount of a TnTuORF peptide or a fragment(s) thereof present in the sample.

Also included in the kit may be a device for sample analysis comprising a disposable testing cartridge with appropriate components (markers, antibodies and reagents) to carry out sample testing. The device will conveniently include a testing zone and test result window. Immunochromatographic cartridges are examples of such devices. See for example U.S. Pat. Nos. 6,399,398; 6,235,241 and 5,504,013.

Alternatively, the device may be an electronic device which allows input, storage and evaluation of levels of the measured marker against control levels and other marker levels. US 2006/0234315 provides examples of such devices. Also useful in the invention are Ciphergen's Protein Chip® which can be used to process SELDI results using Ciphergen's Protein Chip® software package.

Clinical Utility of TnTuORF Peptides

The clinical diagnosis of cardiac disorders including acute coronary syndromes (ACS) relies heavily on circulating diagnostic biomarkers such as cardiac troponin, including Troponin T and Troponin I. However, delays in detectable changes in circulating troponin, even with highly sensitive (hs) assays, results in clinical uncertainty in a significant number of patients presenting with a suspected cardiac disorder. Thus, identification of novel biomarkers that may provide early information in cardiac disorders is of major importance. Applicants provide here the first evidence that an upstream open reading frame (uORF) peptide is present as a distinct chemical entity in the human circulation. This uORF is derived from cardiac troponin T (TnTuORF) and is present in normal healthy individuals. The highest plasma levels of TnTuORF were observed in patients with cardiac disorders other than myocardial infarction and unstable angina, including but not limited to, for example, atrial fibrilation, heart failure, pericarditis and disorders of nerve conduction, and can therefore be used in the assays, methods and kits of the present invention to predict or diagnose a cardiac disorder in a subject.

The invention will now be illustrated with respect to the following non-limiting examples.

EXAMPLES

Example 1

Methods and Materials

Chemicals

Synthetic human TnTuORF, TnTuORF(Tyr), TnTuORF (Cys) and amino acids 1-7 of the signal peptide of vesicular integral membrane protein 36 (VIP36sp(1-7)) were synthesised by Mimotopes (Melbourne, Australia) at greater than 95% purity by mass spectrometry and high performance liquid chromatography (HPLC). All other synthetic or purified proteins were purchased from Hytest (Turku, FI), Peptide Institute (Osaka, Japan) or Sigma-Aldrich (St Louis, USA).

Human TnTuORF Assay Development

Assessment of the 5' region upstream of the major open reading frame of human cardiac troponin T (NCBI Accession NG_007556) identified a putative 12 amino acid peptide (full amino acid sequence MAPEGWVIVVIS; SEQ ID NO:1) encoded 1,512 bp upstream of the major open reading frame (ORF) initiation site, with a Kozak score of +2 and a high likelihood of being efficiently translated (FIG. 1). This sequence was not seen in fast (NCBI Accession NG_013085) or slow (NCBI Accession NG_011829) human skeletal troponin T. However, examination on the NCBI BLAST search engine revealed one partial sequence, the first 7 amino acids of the signal peptide of vesicular integral membrane protein 36 (sequence MAAEGWI) as displaying homology (Fiedler et al. (1994) *EMBO J.* 13:1729-1740). Applicants have previously shown that signal peptides are present in the human circulation (Siriwardena et al. (2010) *Circulation* 122:255-264; Pemberton et al. (2012) *Clin. Chem.* 58:757-767) and so the detection antibody was directed towards the amino terminus of TnTuORF, and VIP36sp(1-7) peptide was assessed for potential interference. Antibodies specific for the amino terminus of TnTuORF were developed according Applicants previous protocols (Siriwardena et al. (2010) *Circulation* 122:255-264; Pemberton et al. (2012) *Clin. Chem.* 58:757-767). Briefly, synthetic TnTuORF(Cys) was coupled to keyhole limpet hemocyanin (KLH) and injected intradermally into four New Zealand White rabbits over 5-6 sites. Rabbits were bled 11-13 days after injection and the procedure repeated 4-6 weekly until adequate antiserum (r244) titres were obtained.

Preparation of $^{125}$I-Radiolabelled Human TnTuORF(Tyr)

Human TnTuORF(Tyr) (2.5 pg) was iodinated using 0.5 mCl Na-$^{125}$I in the presence of 5 µg chloramine T in 5 µL of 0.5 M phosphate buffer, pH 7.3 for 15-20 s. The reaction was stopped by addition of 50 pg cysteine HCl in a further 5 µL of phosphate buffer. The resulting iodinate was loaded onto a 10 cm RP300 Brownlee HPLC column (Applied Biosystems, San Jose, Calif.) and pure TnTuORF($^{125}$I-Tyr) eluted with a gradient of 0% to 60% acetonitrile in 0.1% trifluoroacetic acid (TFA) over 15 min at a flow rate of 1 mL/min.

TnTuORF and Cardiac Marker Assays

For TnTuORF assay, antisera r244 was used at a final dilution of 1:15,000. All radioactive trace and antiserum were diluted in immunoassay buffer (Siriwardena et al. (2010) *Circulation* 122:255-264). Plasma samples and standards were diluted 1:3 in assay buffer. The assay incubate consisted of 50 uL of sample or standard (0-13,000 pg/mL TnTuORF peptide) mixed with 50 uL of antibody at 1:5000 dilution, mixed and left to incubate for 22 hours at 4° C. 50 uL of iodinated TnTuORF(Tyr) tracer (~3000 cpm) was then added, tubes mixed and left to incubate for a further 22 hrs at 4° C. Free and bound TnTuORF were then separated by solid-phase second antibody method (donkey anti-rabbit SacCel, Immunodiagnostic Systems, Boldon, UK). Sac-Cel (500 uL) in 2% polyethylene glycol/phosphate buffer (final Sac-Cel concentration 5%) was added to each tube and left to incubate at room temperature for 30 minutes. Tubes were then centrifuged at 2800×g for 15 minutes, the supernatant decanted and pellet counted in a Gammamaster counter (LKB, Uppsala, Sweden). Assessment of hemolysis determined that TnTuORF was not altered up to a haemoglobin concentration of up to 1.5 g/L or by plasma lipid content up to 2.0 g/L. NT-proBNP was determined by in-house immunoassay (Richards et al. (2006) *J. Am. Coll. Cardiol.* 47:52-60; Wright et al. (2003) *J. Am. Coll. Cardiol.* 42:1793-1800). High sensitivity TnT was determined on an Elecsys 2010 analyser (Roche Diagnostics) with a 99$^{th}$ percentile cut-off of 14 pg/mL. All hsTnT results were submitted to Penzberg during the worldwide reassessment of hsTnT by Roche (Apple et al. (2012) *Clin. Chem.* 58:1599-1600) and only 3 were reported to require adjustment. TnI was determined by a late generation assay (Abbott Architect) with a 99$^{th}$ percentile cut-off of 0.03 ug/L.

Human Plasma Sample Collection

Human plasma samples were obtained from four study groups (demographic data given in Tables I and II) in accordance with ethical protocols approved by the Health and Disabilities Ethics Committee of the Ministry of Health, New Zealand. All participants gave informed consent before recruitment and all investigations conform to the principles of the Declaration of Helsinki. Plasma samples were drawn from: (i) healthy volunteers with no evidence/history of cardiovascular, endocrine or psychiatric illness (n=109), (ii) patients undergoing clinically indicated cardiac catheterisation (n=16), (iii) patients with documented ST-elevation myocardial infarction (n=4) and (iv) an ACS cohort (n=502).

For this study, patients presenting to Christchurch Hospital with the primary complaint of chest pain <4 hours duration were offered recruitment into our prospective, observational study known as Signal Peptides in Acute Coronary Events (SPACE, http://www.anzctr.org.au, ACTRN12609000057280). Patients with the primary complaint of acute chest, epigastric, neck, jaw or arm pain suspicious of ACS, without obvious non-cardiac origin, and lasting ≥20 minutes were enrolled in accordance with guideline definitions (Leupker et al. (2003) *Circulation* 108:2543-2549). More general/atypical symptoms (such as fatigue, nausea, vomiting, sweating and faintness) were not used as inclusion criteria. The adjudicated diagnosis of acute MI was diagnosed in accordance with the 2007 ESC/ACCF/AHA/WHF taskforce guidelines (Thygesen et al. (2007) *Circulation* 352:98-100) by two independent cardiologists with access to all clinical data but not TnTuORF. The biochemical component of diagnosis used an elevation of plasma cTnI ≥0.03 ug/L within 24 hours of admission. All relevant clinical, demographic and diagnostic parameters were collected at index admission, with follow up at 45 and 365 days.

TABLE I

Demographic data (mean ± SD) for patient groups (i)-(iii)

| | Normal Controls (n = 109) | Catheterisation (n = 16) | STEMI (n = 4) |
|---|---|---|---|
| Age (yrs) | 43.9 ± 15.2 | 65.6 ± 10.6 | 61.3 ± 2.9 |
| Male | 40 (37%) | 12 (75%) | 3 (75%) |
| BMI (kg · m$^2$) | 26.2 ± 4.3 | 29.4 ± 6.4 | 26.5 ± 6.6 |
| Hypertension | 27 (21.6%) | 10 (63%) | 2 (50%) |
| Diabetes | 6 (5.5%) | 4 (25%) | 0 (0%) |
| Hyperlipidemia | 18 (17%) | — | 0 (0%) |
| GFR (mL/min/1.73 m$^2$) | 83.0 ± 13.5 | 61.9 ± 24.7 | — |

All patients had blood drawn into chilled Vacutainer tubes containing 1.8 mg/mL Na$^3$-EDTA (Becton-Dickinson). Samples were centrifuged within 2 hrs of drawing and plasma stored at −80° C. For group (i), single samples were taken (after an overnight fast) from a forearm vein, immediately centrifuged to prepare plasma and stored at −80° C. Patients in group (ii) were catheterised via the left femoral artery and had blood drawn from regional vascular sites (femoral vein, renal vein, hepatic vein, inferior vena cava, jugular vein, cardiac coronary sinus and pulmonary artery). Entry and exit femoral arterial samples were taken for comparison. STEMI patients in group (iii) had forearm venous samples taken at hospital presentation at the following times after presentation: 0, 0.5 hr, 1 hr, 2 hr, 4 hr, 8 hr, 12 hr, 24 hr, 48 hr and 72 hr. Patients in group (iv) had blood samples drawn at hospital presentation, and at 1, 2 and 24 hours post-presentation.

TABLE II

Demographic data (mean ± SD) for patient group (iv)

| | Myocardial infarction (MI) | Unstable angina pectoris (UA) | Other cardiac disorder | Non-cardiac chest pain | All patients | P-value |
|---|---|---|---|---|---|---|
| Patient no. (%) | 114 (23) | 40 (8) | 26 (5) | 322 (64) | 502 (100) | |
| Gender no. (%) | | | | | | |
| Male | 77 (15) | 26 (5) | 16 (3) | 182 (37) | 302 (60) | |
| Female | 37 (7) | 14 (3) | 10 (2) | 139 (28) | 200 (40) | |
| Age, yrs | | | | | | |
| Male | 66.0 ± 13.1 | 64.0 ± 8.3 | 65.0 ± 14.1 | 59.0 ± 13.7 | 62.2 ± 13.4 | |
| Female | 78.0 ± 12.7 | 66.0 ± 7.6 | 72.5 ± 6.7 | 68.0 ± 13.5 | 68.3 ± 12.9 | <0.001 |
| Analytes | | | | | | |
| 24 hr TnI (ug/L) | | | | | | |
| Male | 7.8 ± 15.6 | 0.02 ± 0.03 | 0.3 ± 1.2 | 0.01 ± 0.02 | 2.1 ± 8.6 | <0.001 |
| Female | 6.1 ± 11.9 | 0.01 ± 0.01 | 0.2 ± 0.6 | 0.01 ± 0.01 | 1.2 ± 5.6 | <0.001 |
| Chol (mg·dL$^{-1}$)ψ | 181.1 ± 60.3 | 175.2 ± 45.2 | 173.7 ± 31.3 | 186.8 ± 59.3 | 183.5 ± 57.4 | |
| HDL (mg·dL$^{-1}$)ψ | 39.5 ± 12.5 | 38.6 ± 10.7 | 40.3 ± 13.8 | 39.6 ± 12.3 | 39.5 ± 12.3 | |
| LDL (mg·dL$^{-1}$)ψ | 116.3 ± 38.8 | 106.7 ± 37.7 | 100.7 ± 25.6 | 115.5 ± 36.9 | 114.2 ± 37.1 | |
| Trig (mg·dL$^{-1}$)§ | 159.1 ± 83.0 | 149.1 ± 90.7 | 141.6 ± 57.9 | 166.1 ± 182.9 | 161.3 ± 148.3 | |
| Risk factor (%) | | | | | | |
| Hypertension | 78 (16) | 33 (7) | 20 (4) | 192 (38) | 323 (65) | |
| Diabetes | 19 (4) | 9 (2) | 4 (1) | 43 (8) | 75 (15) | |
| BMI (kg·m$^2$) | 28.4 ± 5.2 | 27.6 ± 4.3 | 28.4 ± 5.5 | 28.5 ± 6.1 | 28.4 ± 5.7 | |
| Current smoker | 16 (3.5) | 2 (0.5) | 0 (0) | 44 (9) | 62 (13) | |
| Ever smoker | 56 (11) | 21 (4) | 19 (4) | 157 (31) | 253 (50) | |
| History (%) | | | | | | |
| CVD | 78 (15) | 36 (7) | 13 (3) | 199 (40) | 326 (65) | |
| MI | 36 (7) | 20 (4) | 10 (2) | 99 (20) | 165 (33) | |
| CABG | 9 (1.5) | 6 (1) | 3 (0.5) | 35 (7) | 53 (10) | |
| Hyperlipidaemia | 62 (12) | 34 (7) | 14 (3) | 193 (38) | 303 (60) | |
| Angina | 48 (10) | 30 (6) | 17 (3) | 158 (31) | 253 (50) | |
| Heart failure | 10 (2) | 4 (1) | 2 (0.5) | 33 (6.5) | 49 (10) | |
| ECG Findings | | | | | | |
| LBBB | 3 (1) | 1 (0) | 1 (0) | 7 (2) | 12 (4) | |
| ST-elevation | 23 (6) | 0 (0) | 2 (1) | 0 (0) | 25 (7) | |
| ST-depression | 10 (3) | 1 (0) | 3 (0.5) | 2 (0.5) | 16 (4) | |
| T-wave inversion | 20 (4) | 5 (1) | 6 (1) | 30 (7) | 61 (13) | |
| No change | 58 (9) | 33 (6) | 14 (3) | 283 (54) | 388 (72) | |

ψ= to convert mg·dL$^{-1}$ cholesterol to mmol/L, multiply by 0.0259
§= to convert mg·dL$^{-1}$ triglycerides to mmol/L, multiply by 0.0113

Purification of TnTuORF Peptide from Human Plasma

In order to purify immunoreactive TnTuORF detected in human plasma, anti-TnTuORF IgG from r244 was purified via antigen affinity chromatography on a SulfoLink™ column (Pierce Biotechnology, IL) coupled with TnTuORF (Cys). 2 mL of r244 neat antiserum was diluted 1:1 v/v with PBS (pH 7.2) and run through the SulfoLink™ column. Bound antibody was eluted with 0.1M glycine (pH 2.5) and dialysed against 3 washes of 0.1M phosphate buffer. Purified r244 anti-TnTuORF IgG was then coupled to Protein A agarose gel (Pierce Biotechnology, IL) prepared according to the manufacturer's instructions. To obtain pure TnTuORF, 100 mL of ST-elevation MI patient plasma was diluted 1:1 v/v with PBS (pH 7.2) and run through the Protein A/r244-IgG column under gravity at room temperature for 2 hours. The column was then washed with 0.1M PBS/0.5M NaCl (pH 7.2) and eluted with 0.1M glycine (pH 2.5). 1 mL fractions were collected and an aliquot diluted 1:10 v/v with immunoassay buffer and submitted to specific immunoassay to determine the quantum of purified TnTuORF. Raw glycine elution fractions were immediately stored at −80° C. until assessment by HPLC.

High Performance Liquid Chromatography (HPLC)

Immunoaffinity purified TnTuORF peptide in 0.1M glycine was directly loaded onto a reverse phase (RP) HPLC column (Phenomenex, Torrance, Calif.) at 40° C. and eluted with a gradient of 10-40% acetonitrile/0.1% TFA over 30 minutes at a flow rate of 1 mL/minute. Fractions were collected at 1 minute intervals, and aliquots subjected to TnTuORF immunoassay. Immunoreactive fractions were dried under air and then subjected to size exclusion (SE) HPLC on a G2000 silica column (Toyosoda, JP) with an isocratic gradient of 60% acetonitrile/0.1% TFA at a flow rate of 0.25 mL/minute. Fractions were collected at 1 minute intervals and interrogated by immunoassay as for RP-HPLC to determine approximate molecular size. RP-HPLC was calibrated with synthetic TnTuORF peptide after immunopurified TnTuORF elution. SE-HPLC runs were calibrated with cytochrome C (Mr 12,000), aprotinin (Mr 6,500), CNP22 (Mr 2,200) and angiotensin II (Mr 1,045) peptides.

Statistics

Results are presented as mean±SD. Comparison of means was carried out using paired, two tailed Students t-test where appropriate. Relational analysis of plasma analyte concentrations using Spearman rank order correlation testing and receiver operated curve (ROC) analysis were carried out using SPSS v17. For ROC curve generation and biomarker panel comparisons, biomarker data were analysed as standardised variables (z-scores). In all cases, the standardised variable was derived from the maximum biomarker value obtained from the t=0, 1 and 2 hour samples, ie. the maximum of the 3 values. In all analyses, a P-value <0.05 was considered significant.

Example 2

Identification of Endogenous TnTuORF in Human Plasma

Figure 3:
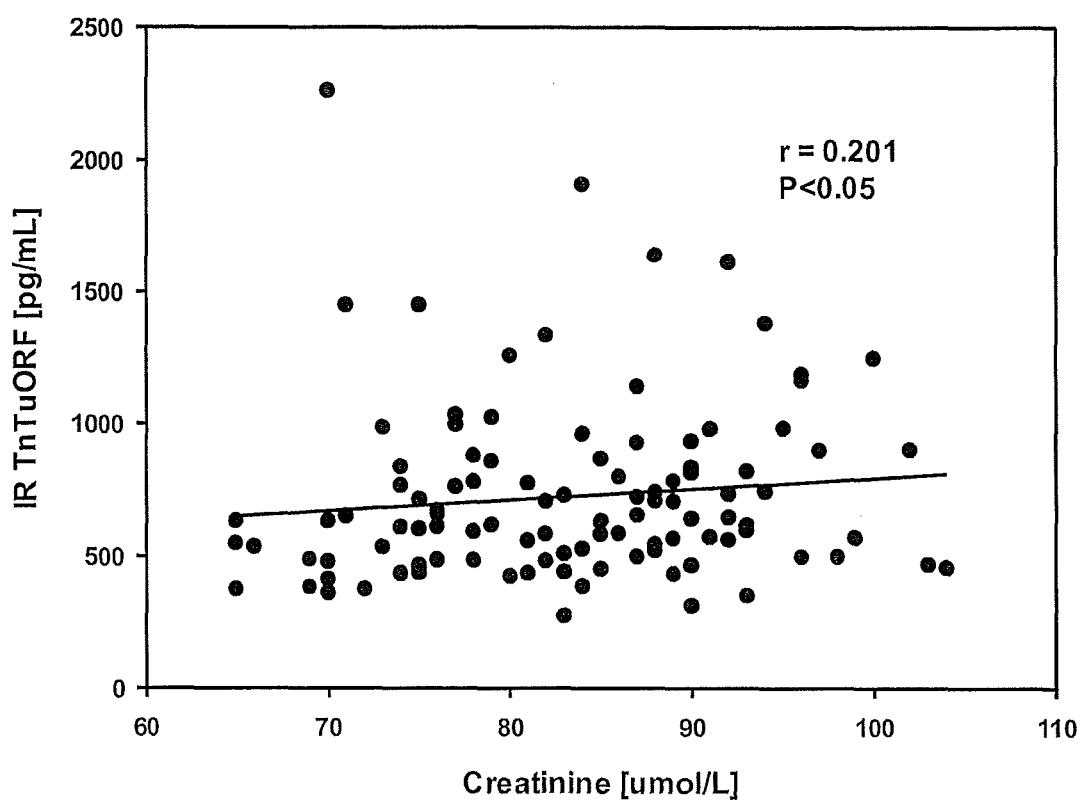
FIG. 3 shows concentrations of immunoreactive (IR) TnTuORF in 109 normal, healthy volunteer plasma samples as demonstrated by a statistically significant (r=0.201, P<0.05 by Spearman Rank correlation analysis) negative correlation with Creatinine.

Polyclonal antibody r244 directed towards the amino terminus of TnTuORF yielded a sensitive, specific radioimmunoassay (FIG. 2), with a mean zero binding of 31±3%, sample detection limit of 26±6 pg/mL, $ED_{50}$ of 458105 pg/mL and a working range of 130-3900 pg/mL in which the intra-assay coefficient of variation (CV) was <10% over 25 assays. Inter-assay CVs were 14% at 1300 pg/mL and 15% at 747 pg/mL. The cross-reactivity of antisera 244 with relevant endogenous peptides, especially cardiac troponin T, troponin I and VIP36sp(1-7) and well known medications was negligible (Table III). Initial assessment confirmed that TnTuORF immunoreactivity was present in human plasma from peripheral blood collected into $Na^3$-EDTA and that it diluted in parallel with the synthetic standard curve (FIG. 2). Immunoreactive TnTuORF levels in normal human venous plasma (mean±SD) were 725±340 pg/mL (range 273-2260 pg/mL, $99^{th}$ percentile of upper limit of normal range=1885 pg/mL); immunoreactivity was detected in every sample. TnTuORF concentrations were significantly higher in men (825±403 pg/mL vs. 666±285 pg/mL, P=0.018) and had a significant biochemical correlation only with plasma creatinine (r=0.201, P=0.036, FIG. 3). Concomitant hsTnT levels, age, blood pressures and BMI had no significant association with TnTuORF. Corresponding hsTnT levels were 6.0±2.4 pg/mL (range 3.0-14.9 pg/mL) and immunoreactivity was present in 49% of samples (53/109). hsTnT levels tended to be higher in men (6.6±2.4 pg/mL vs. 5.5±2.3 pg/mL) and correlated significantly with age (r=0.328, P=0.017).

TABLE III

Cross reactivity data of r244 rabbit anti-human TnTuORF antiserum

| Peptide/Drug | Cross reactivity with TnTuORF antiserum (%) |
|---|---|
| TnTuORF | 100 |
| VIP36sp(1-7) | <0.3 |
| Cardiac Troponin T | <0.01 |
| Cardiac Troponin I | <0.01 |
| hFABP | <0.01 |
| CK-MB | <0.01 |
| proBNP(1-13) | <0.001 |
| proBNP(1-76) | <0.001 |
| proANP(1-30) | <0.003 |
| ANP | <0.002 |
| BNP | <0.003 |
| Endothelin 1 | <0.003 |
| Angiotensin II | <0.003 |
| Angiotensin(1-7) | <0.01 |
| Urotensin II | <0.003 |
| CNP22 | <0.004 |
| Clopidigrel | 0 |

TABLE III-continued

Cross reactivity data of r244 rabbit anti-human TnTuORF antiserum

| Peptide/Drug | Cross reactivity with TnTuORF antiserum (%) |
|---|---|
| Morphine | 0 |
| Aspirin | 0 |

All peptides are human forms.

Example 3

Immunoreactive TnTuORF Release into the Circulation

Figure 4:
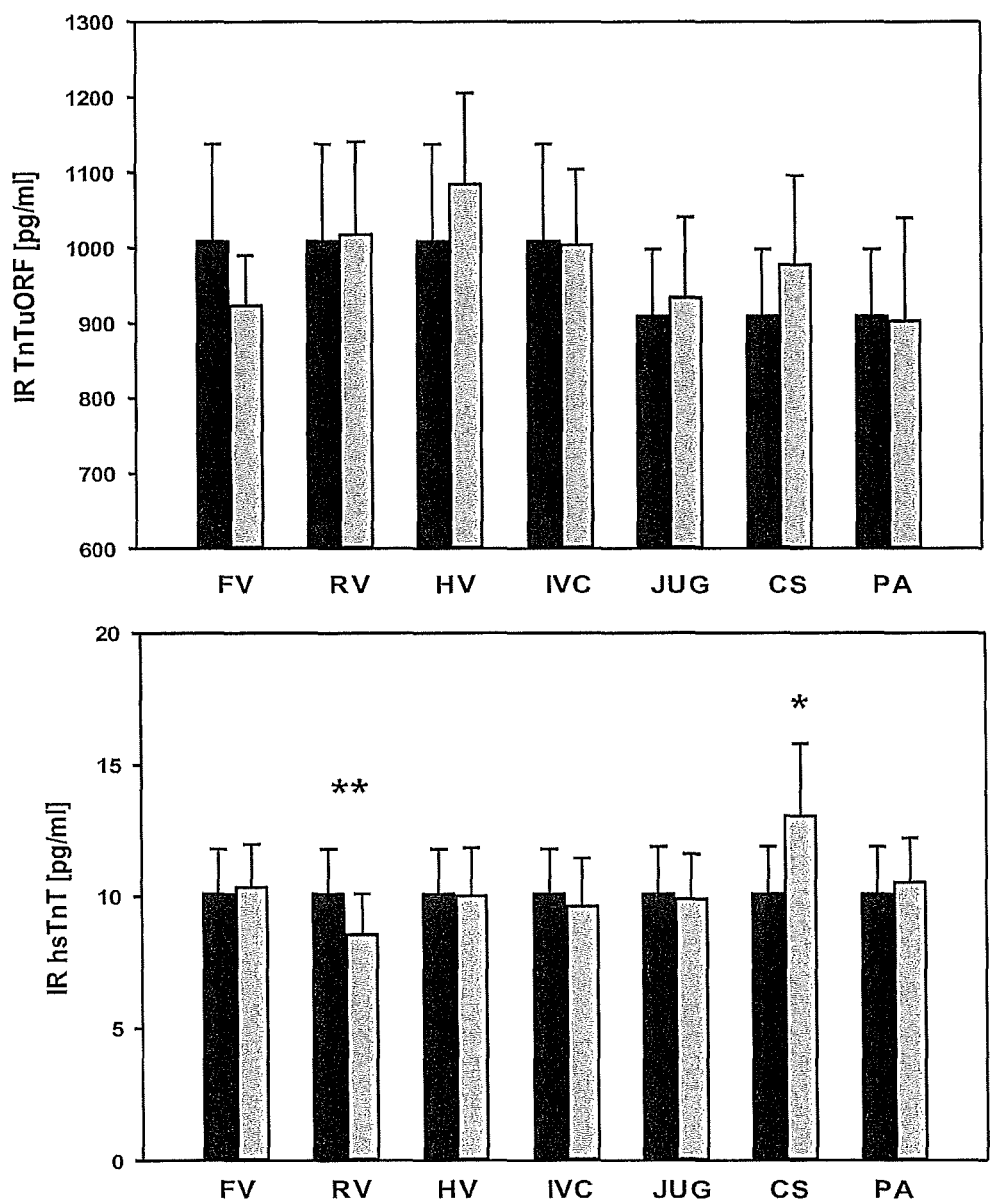
FIG. 4 shows regional arterial-venous concentrations of IR TnTuORF (upper panel) and immunoreactive hsTnT (lower panel) in 16 patients undergoing clinically indicated cardiac catheterisation. Venous concentrations are grey bars, whereas dark bars are time matched arterial samples for comparison of potential organ contribution to circulating levels. FV=femoral vein, RV=renal vein, HV=hepatic vein, IVC=inferior vena cava, JUG=jugular vein, CS=cardiac coronary sinus, PA=pulmonary artery. Bars are Mean±SD, *=P<0.05, **=P<0.01 by paired t-test.

The form of TnT used for the diagnosis of MI is thought to be cardiac specific (Thygessen et al. (2012) *Circulation* 126:2020-2035). In line with this, Applicants anticipated that TnTuORF levels would be higher in blood draining the heart (i.e. in cardiac coronary sinus samples) than in blood supplying the heart (i.e. arterial samples). Coronary sinus plasma tended to contain higher concentrations of immunoreactive TnTuORF, compared with simultaneously drawn arterial plasma samples (978.2±118.1 pg/mL vs. 908.7±88.9 pg/mL, Mean±SD, P=0.472, FIG. 4). However, elevated venous levels of TnTuORF were also observed across the hepatic vein, whereas there tended to be reduced TnTuORF levels across the femoral vein. In comparison, hsTnT levels were significantly elevated in cardiac coronary sinus plasma samples (13.1±2.7 pg/mL vs. 10.1±1.8 pg/mL, P=0.019). Renal venous levels of hsTnT were significantly lower compared with arterial levels (8.6±1.5 pg/mL vs. 10.1±1.7 pg/mL, P=0.002, FIG. 4). Thus, the regional plasma profiles of TnTuORF and cTnT differed with respect to gradients of net production and clearance across organs.

Example 4

Analysis of Immunoreactive Species Detected by RIA

Purified TnTuORF was prepared from 100 mL of plasma by immunoaffinity purification and then subjected to further identification by RP-HPLC and SE-HPLC coupled to immunoassay. Primary RP-HPLC identified two major immunoreactive peaks, the second of which eluted consistent with synthetic TnTuORF peptide (peak II, FIG. 5A). On SE-HPLC, RP-HPLC derived peak II eluted at approximately 1.5K molecular weight, whereas peak I eluted at approximately 1K molecular weight (FIG. 5B). Taken together, these results suggest immunoreactive TnTuORF is present in human plasma as (i) 12 amino acid intact and (ii) carboxyl terminus shortened forms, including MAPEGWVIVVI (SEQ ID NO: 2), MAPEGWVIVV (SEQ ID NO: 3) or MAPEGWVIV (SEQ ID NO: 4).

The Applicants will perform further characterisation of circulating TnTuORF peptide using tandem Ms/MS to confirm the sequence and degradation of this peptide.

Example 5

TnTuORF Peptide in STEMI Patients

Figure 6:
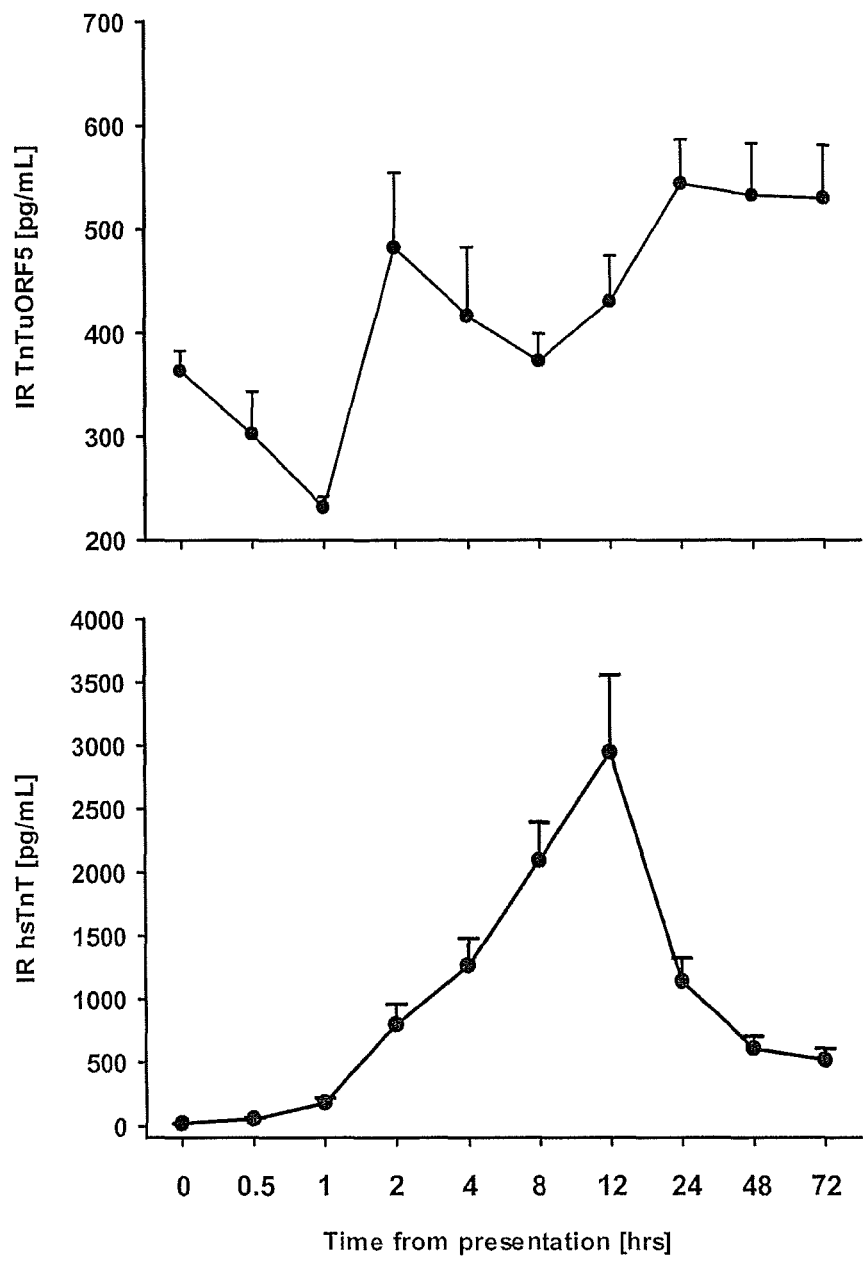
FIG. 6 shows concomitant immunoreactive (IR) concentrations of TnTuORF (panel A) and hsTnT (panel B) in the venous blood of 4 ST-elevation MI patients from hospital presentation to 72 hours post presentation. Data are Mean±SD.

Having established that immunoreactive TnTuORF is present in the human circulation, Applicants sought to determine the clinical utility of circulating TnTuORF as a diagnostic biomarker of acute cardiac ischemia resulting in myocardial infarction. In four patients with documented ST-elevation myocardial infarction (STEMI), whose symptom onset was less than four hours before presentation, venous concentrations of TnTuORF tended to decrease 4-5 hours after symptom onset and increased back to a plateau by 24 hours (FIG. 6A), Average concentrations by 5 hours after symptom onset were almost half those seen in normal controls and did not return fully to that range by 72 hours. This profile clearly differs from that of hsTnT which rises sharply in plasma in STEMI (FIG. 6B).

Example 6

TnTuORF Peptide in a Prospective, Observational Study of Patients Presenting with Chest Pain To assess the potential of TnTuORF measurement to assist in the diagnosis of ACS, Applicants undertook a prospective, observational study of 502 patients presenting consecutively with the primary complaint of chest pain of suspected cardiac origin. Patient demographic and analyte data are given in Table II. Approximately 23% of patients had final adjudicated diagnosis of myocardial infarction (MI). Presentation TnTuORF concentrations did not have any utility to diagnose either acute MI (ROC AUC=0.46, P=NS) or unstable angina (UA, ROC AUC=0.47, P=NS), but had good ability to diagnose patients with cardiac disorders other than ACS (AUC=0.79, P<0.001, FIG. 7) which was more accurate than NTproBNP (AUC=0.72, P<0.001). Accordingly, maximal concentrations of TnTuORF within two hours of presentation were significantly higher in patients with non-MI, non-UA cardiac disorders, compared with all other patients groups (1159±429 pg/mL vs. 778±353 pg/mL, P<0.001). Furthermore, when TnTuORF was added to heart rate and haemoglobin (Hb) concentration, the AUC for the diagnosis of alternate cardiac disorders improved to 0.83 (P<0.001, FIG. 7). hsTnT and TnI both had excellent diagnostic ability to diagnose non-ST elevation MI (NSTEMI) with ROC curves of 0.95 and 0.97, respectively (NSTEMI n=96, both P<0.001). In comparison the product ratio of TnI×hsTnT/TnTuORF (designated here as 'TroponinPLUS™') gave an AUC of 0.97, P<0.001, FIG. 8). In absolute terms, within two hours of presentation, hsTnT detected 94% of NSTEMI patients (90/96) whereas TnI detected 92% (88/96), although this improved sensitivity exhibited by hsTnT came at the cost of increased false positives (hsTnT positive non-MI patients=68 versus TnI positive non-MI patients=32). In comparison, TroponinPLUS detected 98% of NSTEMI patients within two hours (94/96) and generated 63 non-MI positive results. Thus, compared with hsTnT alone, the TroponinPLUS ratio increased by 4% the number of MI patients detected with two hours, and reduced the false positive rate by 7%.

With respect to prognosis, TroponinPLUS predicted mortality at 1 year (AUC=0.74, P<0.001), slightly better than hsTnT and TnI alone (AUC 0.72 and 0.71, respectively) but did not improve on either troponin T or troponin I to predict readmission with MI or CHF within one year. Addition of single inpatient 24 hour TnTuORF concentration to matched NTproBNP improved the ROC curve for 24 hour NTproBNP alone to predict readmission with acute decompensated heart failure (ADHF) with one year (0.93 vs. 0.91, FIG. 9).

Discussion/Summary

Applicants results are the first demonstration of a uORF peptide as a distinct, separate entity within the circulation. It has previously been reported that a uORF peptide from GR-1A receptor is present in isolate cell cytosolic extracts (Diba et al. (2001) *J. Cell. Biochem.* 81:149-161), the authors did not report it being present in media used in their experiments. Applicants found no evidence on immunoassay or HPLC for TnTuORF in human plasma to be associated with hsTnT; indeed, plasma levels of TnTuORF tended to correlate negatively with hsTnT and TnI. However, Applicants cannot exclude the possibility that TnTuORF associates or binds to other plasma entities, such as autoantibodies or other binding proteins, as has been reported for both TnT and TnI (Eriksson et al. (2005) *N. Engl. J. Med.* 352:98-100; Savukoski et al. (2012) *Clin. Chem.* 58:1040-1048).

In the STEMI patient cohort interrogated (Example 1, Table I), regional plasma concentration analysis revealed the cardiac coronary sinus to contain the highest amount of hsTnT, and this observation is entirely consistent with the cardiovascular diagnostic utility of hsTnT. However, it is notable that 4/16 individuals had elevated hepatic arterio-venous hsTnT gradients, 6/16 had elevated jugular arterio-venous gradients and 11/16 had elevated femoral arterio-venous gradients. It is unlikely that this is related to assay issues as the differentials were always much larger than the assay CV. The relevance of these observations is unclear, but it may potentially contribute to the decreased diagnostic specificity observed with the hsTnT assay, especially in the context of which have been noted as a possible source of false positive troponin T (Jaffe et al. (2011) *J. Am. Coll. Cardiol.* 58:1819-1824). Significantly decreased renal vein concentrations of hsTnT indicate it is likely that the kidney is a major clearance mechanism of hsTnT. With respect to TnTuORF, although Applicants observed an elevated arterio-venous gradient across the cardiac coronary sinus, this was not statistically significant.

Immunopurified TnTuORF eluted on RP- and SE-HPLC systems consistent with intact and carboxyl terminus degraded forms. TnTuORF is therefore comparable to cTnT and cTnI in terms of degradation, but whether similar enzymes or processes account for this is unknown. Importantly, in terms of immunoassay validation, cTnT and cTnI did not cross-react with the TnTuORF antibody or appear on RP- and SE-HPLC profiles. Furthermore, the closest peptide identity found, using BLAST sequence alignment tool, was VIP36sp(1-7). This peptide differs by only two amino acid from the first 7 amino acids of TnTuORF, although it was shown to have <0.3% cross-reactivity the TnTuORF peptide antibody and so minimal potential to interfere with the assay of the present invention. These data suggest that Proline at position 3 in TnTuORF plays a major part in our antibody recognition and assists with maintaining assay specificity, and full characterisation of circulating TnTuORF by tandem MS/MS will be required to confirm the sequence and degradation of this peptide.

Current evidence suggests uORFs are negatively correlated with protein production (Calvo et al, (2009) *Proc. Natl. Acad. Sci.* 106:7507-7512; Vogel et al. (2010) *Mol. Sys. Biol.* 6:400-408; Matsui et al. (2007) *FEBS Letts.* 581:4184-4188) but their actual functional activity has been demonstrated in only a small number of cases. For example, the production of cis-acting peptides by uORFs can reduce the initiation of translation of the downstream major ORF by stalling the ribosome at the end of the uORF (Oyama et al. (2004) *Genome Res.* 14:2048-2052). This evidence, coupled with Applicants observation that venous TnTuORF concentrations initially decreased in patients with documented STEMI prompted Applicants to investigate whether a potentially useful reciprocal relationship might exist between TnTuORF and hsTnT and/or TnI in patients presenting with chest pain suspicious of acute myocardial infarction. As expected, average maximal concentrations of hsTnT and TnI within two hours of presentation were significantly higher in myocardial infarction patients compared with other patient groups. In contrast, the maximal concentration of TnTuORF tended to be lower in myocardial infarction patients and was significantly lower compared with those with other cardiac disorders. Employing TnTuORF as the denominator in a ratio with cardiac Troponin T and Troponin I (Troponin-PLUS™) made improvements to the diagnosis of NSTEMI and prognosis of 1 year mortality as compared with hsTnT measurement alone. Also of interest was the diagnostic performance of TnTuORF in the identification of chest pain patients presenting with cardiac disorders other than myocardial infarction, which could be improved by the addition of heart rate and Hb variables.

Although the invention has been described by way of example, it should be appreciated that variations and modifications may be made without departing from the scope of the invention as defined in the claims. Furthermore, where known equivalents exist to specific features, such equivalents are incorporated as if specifically referred in this specification.

The invention claimed is:

1. A method of predicting a subject's risk of acquiring a cardiac disorder other than myocardial infarction or unstable angina, or of diagnosing a cardiac disorder other than myocardial infarction or unstable angina in a subject, the method comprising:
   (i) measuring a level of a Troponin T upstream open reading frame (TnTuORF) peptide in a biological sample from the subject by detecting binding between the TnTuORF peptide and a binding agent that selectively binds to the TnTuORF peptide to determine a circulating level of the TnTuORF peptide in the subject; and
   (ii) comparing the level of the TnTuORF peptide measured in (i) against a reference circulating level of the TnTuORF peptide from a suitable control population, wherein a higher value for the circulating level of the TnTuORF peptide in the subject compared to the reference level of the TnTuORF peptide in the control population is predictive of the subject acquiring a cardiac disorder other than myocardial infarction or unstable angina, or is indicative of a cardiac disorder other than myocardial infarction or unstable angina, and wherein the Troponin T upstream open reading frame (TnTuORF) peptide consists of the amino acid sequence set forth in any one of SEQ ID NO:1, SEQ ID NO: 2, SEQ ID NO: 3 or SEQ ID NO: 4,
   wherein the cardiac disorder is selected from atrial fibrillation, heart failure, pericarditis, vasovagalsyncope or any combination thereof.

2. The method of claim 1, wherein step (i) comprises measuring the level of the TnTuORF peptide in a first biological sample taken from the subject at a first point in time to determine a first circulating level of the TnTuORF peptide and measuring the level of the TnTuORF peptide in a second biological sample taken from the subject at a later period in time to determine a second circulating level of the TnTuORF peptide; and comparing the first and second circulating levels of the TnTuORF peptide, wherein an increase in the second circulating level of the TnTuORF peptide relative to the first circulating level is indicative of increased risk of acquiring a cardiac disorder other than myocardial infarction or unstable angina, or is indicative of a cardiac disorder other than myocardial infarction or unstable angina and/or of persistence of a cardiac disorder other than myocardial infarction or unstable angina.

3. The method of claim 1 which further comprises identifying in the subject absence or presence of one or more risk factors that are predictive of the subject acquiring a cardiac disorder other than myocardial infarction or unstable angina, or that are indicative of a cardiac disorder other than myocardial infarction or unstable angina in the subject, said risk factors being selected from heart rate, haemoglobin concentration, blood pressure, age, sex, weight, level of physical activity, family history of obesity, family history of diabetes, family history of cardiac events, and levels of circulating Troponin T and Troponin I.

4. A method for monitoring responsiveness of a subject to treatment with a drug or therapy for a cardiac disorder other than myocardial infarction or unstable angina, the method comprising:
   measuring a first level of a Troponin T upstream open reading frame (TnTuORF) peptide in a first biological sample from the subject by detecting binding between the TnTuORF peptide and a binding agent that selectively binds to the TnTuORF peptide;
   (ii) measuring a second level of t h e TnTuORF peptide in a second biological sample obtained from the subject at a later point in time than the first biological sample and after the subject has received treatment with the drug or therapy, by detecting binding between the TnTuORF peptide and the binding agent that selectively binds to the TnTuORF peptide ; and
   (iii) comparing the measured first and second levels of the TnTuORF peptide in, respectively, the first and second samples,
   wherein an increase in the second level of the TnTuORF peptide relative to the first level of the TnTuORF peptide is indicative of a poor response by the subject to the treatment with the drug or therapy, and wherein a decrease in the second level of the TnTuORF peptide relative to the first level of the TnTuORF peptide is indicative of a positive response by the subject to the treatment with the drug or therapy, wherein the TnTuORF peptide consists of the amino acid sequence set forth in any one of SEQ ID NO:1, SEQ ID NO: 2, SEQ ID NO: 3 or SEQ ID NO: 4.

5. The method of claim 1, wherein:
   (a) the control population comprises one or more control subjects that are sex and age-matched to the subject and for which the cardiac disorder is known; or
   (b) the reference level of the TnTuORF peptide is a mean circulating TnTuORF peptide concentration from the control population; or
   (c) the biological sample is a body fluid or a heart tissue sample; or
   (d) the body fluid is selected from venous blood, arterial blood, plasma, serum and interstitial fluid.

6. The method of claim 1 wherein the binding agent that selectively binds to the TnTuORF peptide is selected from: (i) an antibody or antigen binding fragment thereof; (ii) a polyclonal, monoclonal, chimeric or humanized antibody or antigen binding fragment thereof; (iii) a monoclonal antibody or antigen binding fragment thereof; and (iv) a binding agent or antibody that is immobilized to a solid phase.

7. An assay method for determining a level of a Troponin T upstream open reading frame (TnTuORF) peptide in a biological sample from a subject having, or at risk of acquiring, a cardiac disorder other than myocardial infarction or unstable angina, the assay method comprising detecting and quantitatively measuring binding between the TnTuORF peptide and a binding agent that selectively binds to the TnTuORF peptide to determine the level of the TnTuORF peptide in the biological sample from the subject, wherein the TnTuORF peptide consists of the amino acid sequence set forth in any one of SEQ ID NO:1, SEQ ID NO: 2, SEQ ID NO: 3 or SEQ ID NO: 4.

8. The assay method of claim 7, wherein one or more of:
   (a) the assay method comprises:
      measuring a level of the Troponin T upstream open reading frame (TnTuORF) peptide in the biological sample from the subject to obtain a measured level of the TnTuORF peptide; and
      (ii) comparing the measured level of the TnTuORF peptide from (i) to a reference level of the TnTuORF peptide in a biological sample from a suitable control population,
   wherein an increased level of the TnTuORF peptide measured in (i) relative to the reference level of the TnTuORF peptide in the biological sample from the control population in (ii) is predictive of the subject acquiring a cardiac disorder other than myocardial infarction or unstable angina, or is diagnostic of the subject having a cardiac disorder other than myocardial infarction or unstable angina, and further wherein the measuring step comprises detecting binding between the TnTuORF peptide and a binding agent that selectively binds to the TnTuORF peptide; or (b) the assay method comprises a method that is selected from an immunoassay, an enzyme immunoassay, a radioimmunoassay or a chemiluminescence assay; or (c) the binding agent that selectively binds to the TnTuORF peptide is an antibody or antigen binding fragment thereof.

9. A kit for measuring a level of a Troponin T upstream open reading frame (TnTuORF) peptide in a biological sample from a subject having, or at risk of acquiring, a cardiac disorder other than myocardial infarction or unstable angina, comprising a binding agent that selectively binds to the TnTuORF peptide and which can be quantitatively measured upon binding to the TnTuORF peptide, wherein the TnTuORF peptide comprises the amino acid sequence set forth in any one of SEQ ID NO:1, SEQ ID NO: 2, SEQ ID NO: 3 or SEQ ID NO: 4.

10. The kit of claim 9 in which one or more of:

(a) the binding agent that selectively binds to the TnTuORF peptide is an antibody or antigen binding fragment thereof, and (b) the kit further comprises instructions for measuring the level of the TnTuORF peptide in the sample.

11. A Troponin T upstream open reading frame (TnTuORF) peptide binding agent that selectively binds a TnTuORF peptide, wherein the Troponin T upstream open reading frame (TnTuORF) peptide consists of the amino acid sequence set forth in any one of SEQ ID NO:1, SEQ ID NO: 2, SEQ ID NO: 3 or SEQ ID NO: 4.

12. The Troponin T upstream open reading frame (TnTuORF) peptide binding agent of claim 11 which is an antibody that selectively binds the TnTuORF peptide, or an antigen-binding fragment of said antibody.

* * * * *

```
SEQUENCE LISTING

<160> NUMBER OF SEQ ID NOS: 4

<210> SEQ ID NO 1
<211> LENGTH: 12
<212> TYPE: PRT
<213> ORGANISM: Artificial Sequence
<220> FEATURE:
<223> OTHER INFORMATION: uORF

<400> SEQUENCE: 1

Met Ala Pro Glu Gly Trp Val Ile Val Val Ile Ser
1               5                   10

<210> SEQ ID NO 2
<211> LENGTH: 11
<212> TYPE: PRT
<213> ORGANISM: Artificial Sequence
<220> FEATURE:
<223> OTHER INFORMATION: uORF

<400> SEQUENCE: 2

Met Ala Pro Glu Gly Trp Val Ile Val Val Ile
1               5                   10

<210> SEQ ID NO 3
<211> LENGTH: 10
<212> TYPE: PRT
<213> ORGANISM: Artificial Sequence
<220> FEATURE:
<223> OTHER INFORMATION: uORF

<400> SEQUENCE: 3

Met Ala Pro Glu Gly Trp Val Ile Val Val
1               5                   10

<210> SEQ ID NO 4
<211> LENGTH: 9
<212> TYPE: PRT
<213> ORGANISM: Artificial Sequence
<220> FEATURE:
<223> OTHER INFORMATION: uORF

<400> SEQUENCE: 4

Met Ala Pro Glu Gly Trp Val Ile Val
1               5
```

UNITED STATES PATENT AND TRADEMARK OFFICE
CERTIFICATE OF CORRECTION

PATENT NO.         : 9,784,749 B2
APPLICATION NO.    : 15/036748
DATED              : October 10, 2017
INVENTOR(S)        : Jacqueline Amanda Lee et al.

Page 1 of 1

It is certified that error appears in the above-identified patent and that said Letters Patent is hereby corrected as shown below:

Column 37, Line 63 Claim 4:
"measuring a first level of a Troponin T upstream open" should read as --(i) measuring a first level of a Troponin T upstream open--.

Column 38, Line 54 Claim 8:
"measuring a level of the Troponin T upstream open" should read as --(i) measuring a level of the Troponin T upstream open--.

Signed and Sealed this
Second Day of October, 2018

Andrei Iancu
*Director of the United States Patent and Trademark Office*